US010722222B2

(12) United States Patent
Aranyi

(10) Patent No.: US 10,722,222 B2
(45) Date of Patent: Jul. 28, 2020

(54) SURGICAL SYSTEM INCLUDING A PLURALITY OF HANDLE ASSEMBLIES

(71) Applicant: COVIDIEN LP, Mansfield, MA (US)

(72) Inventor: Ernest Aranyi, Easton, CT (US)

(73) Assignee: COVIDIEN LP, Mansfield, MA (US)

( * ) Notice: Subject to any disclaimer, the term of this patent is extended or adjusted under 35 U.S.C. 154(b) by 1577 days.

(21) Appl. No.: 13/715,364

(22) Filed: Dec. 14, 2012

(65) Prior Publication Data

US 2014/0171923 A1    Jun. 19, 2014

(51) Int. Cl.
  *A61B 17/00*    (2006.01)
  *A61B 17/072*   (2006.01)
  *A61B 17/29*    (2006.01)

(52) U.S. Cl.
  CPC ........ *A61B 17/00* (2013.01); *A61B 17/07207* (2013.01); *A61B 2017/0046* (2013.01); *A61B 2017/00367* (2013.01); *A61B 2017/00398* (2013.01); *A61B 2017/00734* (2013.01); *A61B 2017/2927* (2013.01); *A61B 2017/2929* (2013.01)

(58) Field of Classification Search
  CPC .............. A61B 17/00; A61B 17/07207; A61B 2017/00367; A61B 2017/00398; A61B 2017/0046; A61B 2017/00734; A61B 2017/2927; A61B 2017/2929
  See application file for complete search history.

(56) References Cited

U.S. PATENT DOCUMENTS

| 3,120,845 | A | 2/1964 | Horner |
|---|---|---|---|
| D286,422 | S | 10/1986 | Korthoff et al. |
| 5,653,713 | A | 8/1997 | Michelson |
| 5,702,408 | A | 12/1997 | Wales et al. |
| 5,792,165 | A | 8/1998 | Klieman et al. |

(Continued)

FOREIGN PATENT DOCUMENTS

| EP | 2090251 A2 | 8/2009 |
|---|---|---|
| EP | 2116193 A1 | 11/2009 |

(Continued)

OTHER PUBLICATIONS

Detemple, P., "Microtechnology in Modern Health Care", *Med Device Technol.* 9(9):18-25 (1998), (6 pp.).

(Continued)

*Primary Examiner* — Lynsey C Eiseman
*Assistant Examiner* — Jessandra F Hough

(57) ABSTRACT

A surgical system comprising a surgical instrument, a first handle assembly and a second handle assembly is disclosed. The surgical instrument comprises a shaft assembly defining a longitudinal axis, an end effector disposed adjacent a distal portion of the shaft assembly, and a control rod disposed at least partially within the shaft assembly and being disposed in mechanical cooperation with the end effector. Actuation of the control rod effects a function of the end effector. The first handle assembly is configured for selective mechanical engagement with the control rod. The first handle assembly includes a power source associated therewith. The second handle assembly is configured for selective mechanical engagement with the control rod. The second handle assembly is manually operable and is free from association with a power source.

4 Claims, 32 Drawing Sheets

(56) References Cited

U.S. PATENT DOCUMENTS

| | | | |
|---|---|---|---|
| 5,865,361 A * | 2/1999 | Milliman | A61B 17/07207 227/176.1 |
| 7,997,468 B2 | 8/2011 | Farascioni | |
| 8,070,748 B2 | 12/2011 | Hixson et al. | |
| 8,092,493 B2 | 1/2012 | Marczyk | |
| 8,201,721 B2 | 6/2012 | Zemlok | |
| 8,210,412 B2 | 7/2012 | Marczyk | |
| 2006/0058825 A1 | 3/2006 | Ogura et al. | |
| 2007/0039996 A1 | 2/2007 | Mather et al. | |
| 2008/0035701 A1 | 2/2008 | Racenet et al. | |
| 2008/0223903 A1 * | 9/2008 | Marczyk | A61B 17/072 227/175.1 |
| 2009/0206143 A1 | 8/2009 | Huitema et al. | |
| 2011/0009863 A1 | 1/2011 | Marczyk et al. | |
| 2011/0022032 A1 * | 1/2011 | Zemlok | A61B 17/07207 606/1 |
| 2011/0121049 A1 | 5/2011 | Malinouskas et al. | |
| 2011/0215132 A1 | 9/2011 | Aranyi et al. | |
| 2011/0301579 A1 | 12/2011 | Marczyk | |
| 2012/0080336 A1 | 4/2012 | Shelton, IV et al. | |
| 2012/0253116 A1 | 10/2012 | Sniffin et al. | |
| 2013/0214025 A1 | 8/2013 | Zemlok et al. | |
| 2014/0001236 A1 * | 1/2014 | Shelton, IV | A61B 17/07207 227/176.1 |
| 2014/0005654 A1 * | 1/2014 | Batross | A61B 17/320092 606/33 |
| 2014/0107416 A1 * | 4/2014 | Birnkrant | A61B 1/00016 600/110 |

FOREIGN PATENT DOCUMENTS

| | | |
|---|---|---|
| EP | 2263568 A2 | 12/2010 |
| FR | 2 849 589 | 7/2004 |
| JP | 2005118606 A | 5/2005 |
| JP | 2006075376 A | 3/2006 |
| JP | 2007195982 A | 8/2007 |
| JP | 2009090113 A | 4/2009 |
| JP | 201000341 A | 1/2010 |
| JP | 2011-104379 A | 6/2011 |
| WO | WO 1998/37825 | 9/1998 |
| WO | WO 2003/026511 | 4/2003 |
| WO | WO 2009/039506 | 9/2008 |

OTHER PUBLICATIONS

European Search Report EP 06026840.6 dated May 10, 2007, (4 pp.).
European Search Report EP 08251357.3 dated Sep. 29, 2009, (6 pp.).
European Search Report EP 08252703.7 dated Oct. 31, 2008, (4 pp.).
European Search Report EP 08253184.9 dated Feb. 27, 2009, (5 pp.).
European Search Report-partial EP 10251416.3 dated Nov. 2, 2010, (6 pp.).
European Search Report-extended EP 10251416.3 dated Mar. 14, 2011, (12 pp.).
European Search Report EP 10252080.6 dated Apr. 18, 2011, (3 pp.).
International Search Report PCT/US06/21524 dated May 28, 2008, (4 pp.).
U.S. Appl. No. 13/444,228, filed Apr. 11, 2012, for "Apparatus for Endoscopic Procedures" (80 pp.).
U.S. Appl. No. 13/543,931, filed Jul. 9, 2012, for "Surgical Device With Articulation and Wrist Rotation" (36 pp.).
Chinese First Office Action corresponding to counterpart Int'l Appln. No. CN 201310684368 dated Feb. 13, 2017.
Extended European Search Report corresponding to EP 13 19 7184.8, completed Apr. 14, 2015 and dated Apr. 22, 2015; (11 pp).
European Office Action corresponding to counterpart Int'l Appln. No. EP 13 19 7184.8 dated Sep. 30, 2016.
Partial European Search Report corresponding to EP 13 19 7184.8, completed Nov. 4, 2014 and dated Nov. 10, 2014; (7 pp).
European Office Action corresponding to counterpart Int'l Appln. No. EP 13 19 7184.8 dated Aug. 28, 2017.
Australian Examination Report No. 1 corresponding to Int'l Appln. No. AU 2014200793 dated Sep. 2, 2017.
Japanese Office Action corresponding to counterpart Japanese Appln. No. JP 2013-254873 dated Dec. 22, 2017.

* cited by examiner

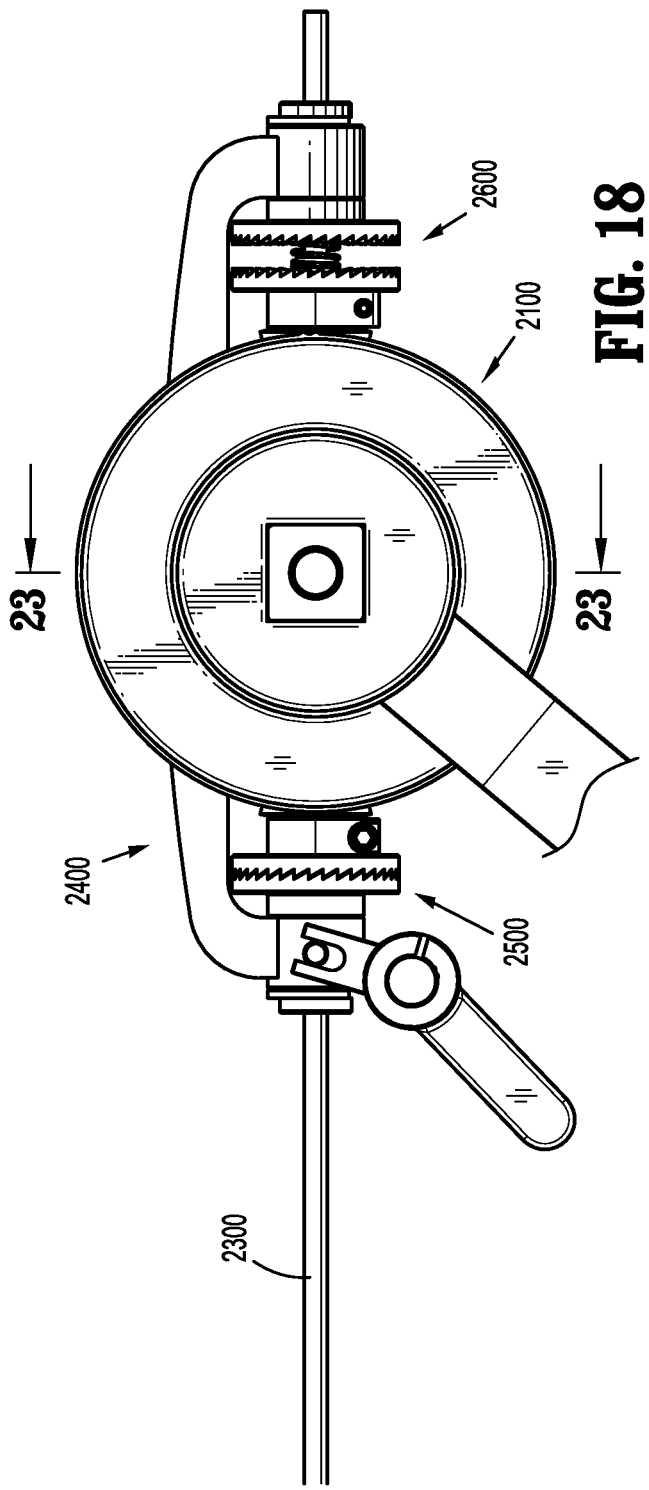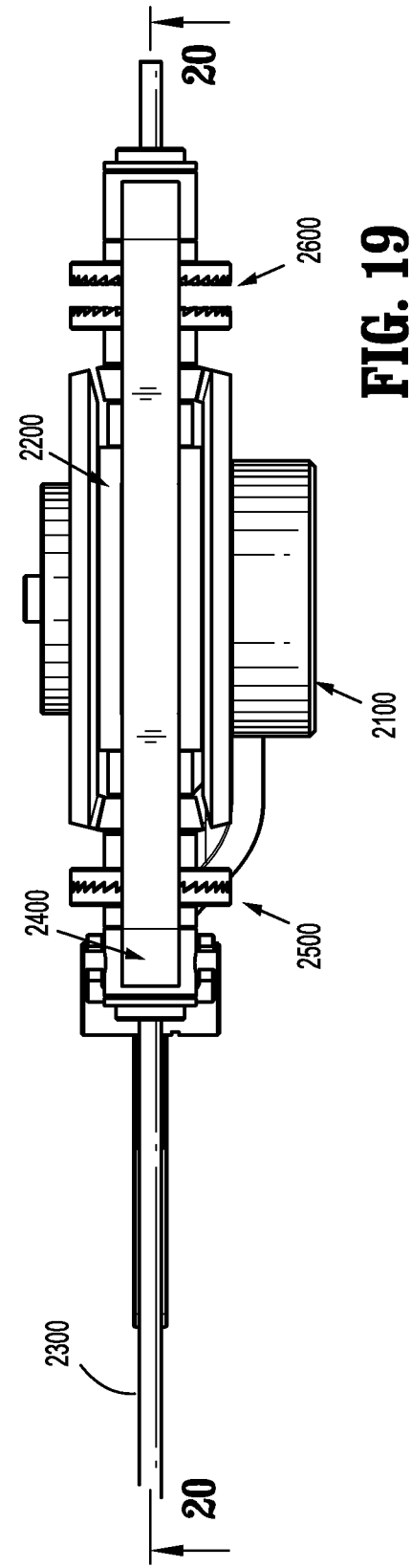
FIG. 18
FIG. 19

SURGICAL SYSTEM INCLUDING A PLURALITY OF HANDLE ASSEMBLIES

BACKGROUND

1. Technical Field

The present disclosure relates to surgical apparatuses, devices and/or systems for performing surgical procedures and methods of use thereof. More specifically, the present disclosure relates to hand-held surgical apparatuses, devices and/or systems configured for use with selectively removable handle assemblies, and handle assemblies for use therewith.

2. Background of Related Art

A number of surgical device manufacturers have developed product lines with proprietary drive systems for operating and/or manipulating electromechanical surgical devices. In many instances the electromechanical surgical devices include a reusable powered handle assembly, and disposable or single use loading units. The loading units are selectively connected to the handle assembly prior to use and then disconnected from the handle assembly following use in order to be disposed of or in some instances sterilized for re-use.

Many of these electromechanical surgical devices are relatively expensive to manufacture, purchase and/or operate. There is a constant desire by manufacturers and end users to develop electromechanical surgical devices that are relatively inexpensive to manufacture, purchase and/or operate.

Additionally, in the event that the powered handle assembly of the electromechanical surgical device should become inoperable or ineffective during a surgical procedure, a desire exists to manually be able to complete or reverse the surgical step.

SUMMARY

The present disclosure relates to a surgical system comprising a surgical instrument, a first handle assembly and a second handle assembly. The surgical instrument comprises a shaft assembly defining a longitudinal axis, an end effector disposed adjacent a distal portion of the shaft assembly, and a control rod disposed at least partially within the shaft assembly and being disposed in mechanical cooperation with the end effector. Actuation of the control rod effects a function of the end effector. The first handle assembly is configured for selective mechanical engagement with the control rod. The first handle assembly includes a power source associated therewith. The second handle assembly is configured for selective mechanical engagement with the control rod. The second handle assembly is manually operable and is free from association with a power source.

In disclosed embodiments, the surgical instrument further comprises a manual articulation control configured to move the end effector at an angle with respect to the longitudinal axis.

In disclosed embodiments, the surgical system further comprises a third handle assembly configured for selective mechanical engagement with the control rod. The third handle assembly is manually operable and is free from association with a power source.

In disclosed embodiments, the second handle assembly includes a switch assembly and a rod. The rod is mechanically engagable with the control rod of the surgical instrument. The switch assembly is configured to control the direction of rotation of the rod. Here, it is disclosed that rotation of the rod in a first direction effects a first function of the end effector, and rotation of the rod in a second direction effects a second function of the end effector. Further, it is disclosed that the second handle assembly includes a first set of gears and a second set of gears. Rotation of the first set of gears, when engaged, causes rotation of the rod in the first direction, and rotation of the second set of gears, when engaged, causes rotation of the rod in the second direction. The switch assembly allows a user to selectively engage one of the sets of gears.

The present disclosure also relates to a surgical system comprising a surgical instrument and a first handle assembly. The surgical instrument comprises a shaft assembly defining a longitudinal axis, an end effector disposed adjacent a distal portion of the shaft assembly, a control rod, and a control assembly. The control rod extends at least partially through the shaft assembly and is disposed in mechanical cooperation with the end effector. Longitudinal translation of the control rod effects a function of the end effector. The control assembly is disposed in mechanical cooperation with the end effector and comprises at least one articulation control including a manually rotatable element. Rotation of the element causes the end effector to move from a first portion where the end effector is substantially parallel to the longitudinal axis to a second position where the end effector is disposed at an angle with respect to the longitudinal axis. The first handle assembly is configured for selective mechanical engagement with the control rod of the surgical instrument. The first handle assembly includes a power source and a drive member. The power source is actuatable to rotatable the drive member about the longitudinal axis.

In disclosed embodiments, the first handle assembly further comprises a rod disposed in mechanical cooperation with the drive member. Rotation of the drive member causes a corresponding rotation of the rod. Here, it is disclosed that rotation of the rod causes longitudinal translation of the control rod.

In disclosed embodiments, the control assembly includes a second articulation control including a second manually rotatable element. Rotation of the second manually rotatable element causes the end effector to move from the first portion where the end effector is substantially parallel to the longitudinal axis to a third position where the end effector is disposed at an angle with respect to the longitudinal axis and at an angle with respect to the second position. The second manually rotatable element is individually operable from the manually rotatable element of the first articulation control.

In disclosed embodiments, the system further comprises a second handle assembly configured for selective mechanical engagement with the control rod of the surgical instrument. The second handle assembly includes a movable handle that is pivotable with respect to a handle housing. Here, it is disclosed that the second handle assembly includes a rod, which is selectively engageable with the control rod of the surgical instrument. Actuation of the movable handle causes rotation of the rod about the longitudinal axis. Further, it is disclosed that rotation of the rod of the second handle assembly about the longitudinal axis causes longitudinal translation of the control rod when the second handle assembly is engaged with the surgical instrument.

It is further disclosed that the second handle assembly includes a switch assembly, which is configured to control the direction of rotation of the rod. It is also disclosed that rotation of the rod in a first direction effects a first function of the end effector, and rotation of the rod in a second direction effects a second function of the end effector. Additionally, it is disclosed that the second handle assembly includes a first set of gears and a second set of gears. Rotation of the first set of gears, when engaged, causes rotation of the rod in the first direction, and rotation of the second set of gears, when engaged, causes rotation of the rod in the second direction. The switch assembly allows a user to selectively engage one of the sets of gears.

The present disclosure also relates to a method of performing a surgical procedure. The method comprises providing a surgical system comprising a surgical instrument, a first handle assembly, and a second handle assembly. The surgical instrument includes an end effector and a shaft. The first handle assembly includes a power source therein. The second handle assembly includes a manually movable handle. The method also includes mechanically connecting the first handle assembly with the surgical instrument, positioning the end effector adjacent target tissue, commencing a surgical procedure by the end effector on the target tissue by actuating the first handle assembly, disconnecting the first handle assembly from mechanical engagement with the surgical instrument, mechanically connecting the second handle assembly with the surgical instrument, and at least one of completing the surgical procedure on the target tissue and reversing a movement of the end effector.

In disclosed embodiments of the method, the end effector remains adjacent the target tissue during the disconnection of the first handle assembly from mechanical engagement with the surgical instrument. Here, it is disclosed that the end effector remains adjacent the target tissue during the mechanical connection between the second handle assembly and the surgical instrument.

It is further disclosed embodiments of the method, the second handle assembly includes a switch assembly, a first set of gears, a second set of gears, and a rod. The rod is mechanically engagable with a control rod of the surgical instrument. The switch assembly is configured to control the direction of rotation of the rod. Rotation of the first set of gears, when engaged, causes rotation of the rod in a first direction, and rotation of the second set of gears, when engaged, causes rotation of the rod in a second direction. The switch assembly allows a user to selectively engage one of the sets of gears.

BRIEF DESCRIPTION OF THE DRAWINGS

Embodiments of the present disclosure are described herein with reference to the accompanying drawings, wherein:

FIG. 18 is a side view of the third handle assembly;

FIG. 19 is a top view of the third handle assembly;

DETAILED DESCRIPTION OF EMBODIMENTS

Figure 1:
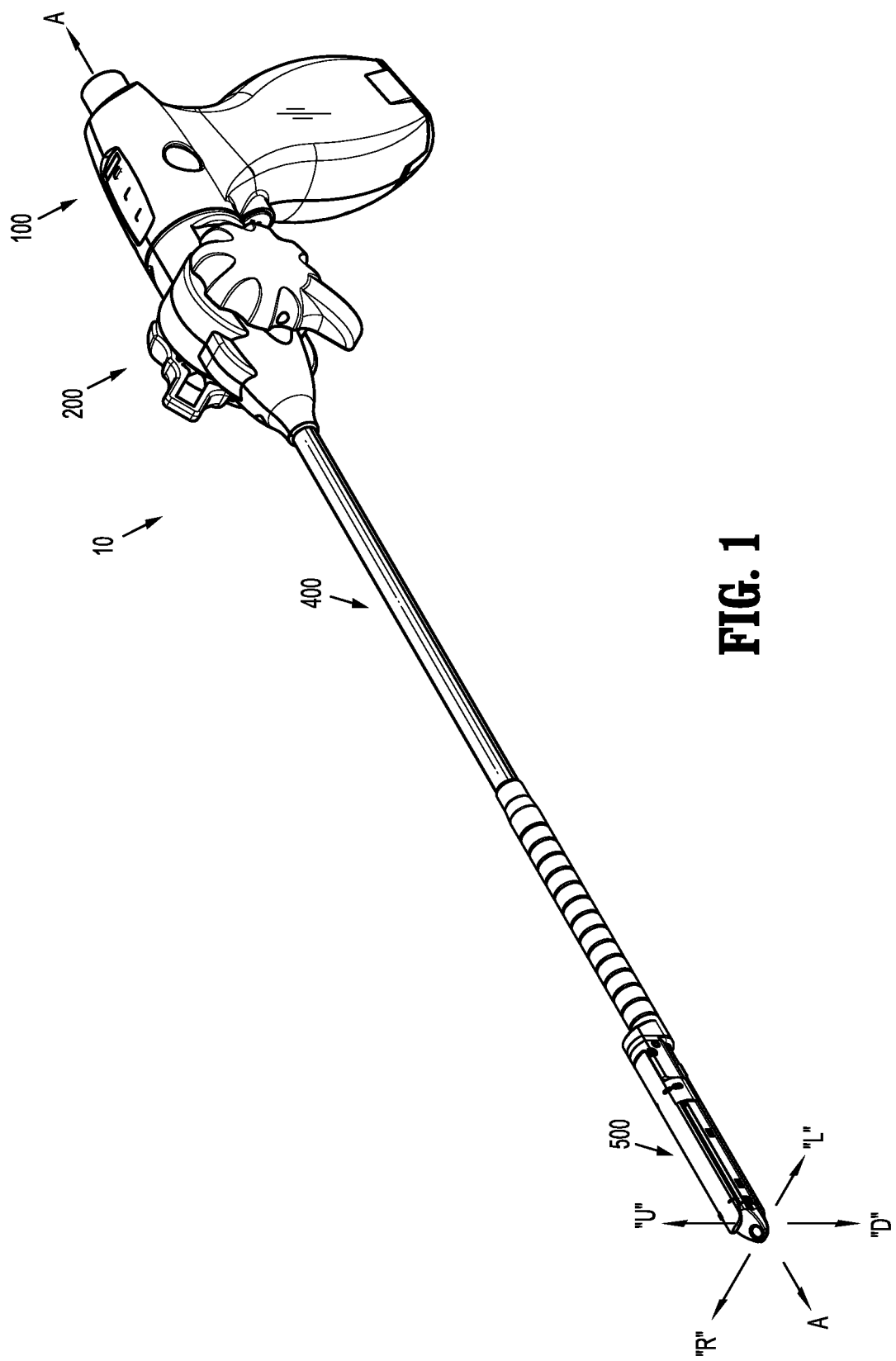
FIG. 1 is a perspective view of a surgical instrument according to embodiments of the present disclosure.
Figure 2:
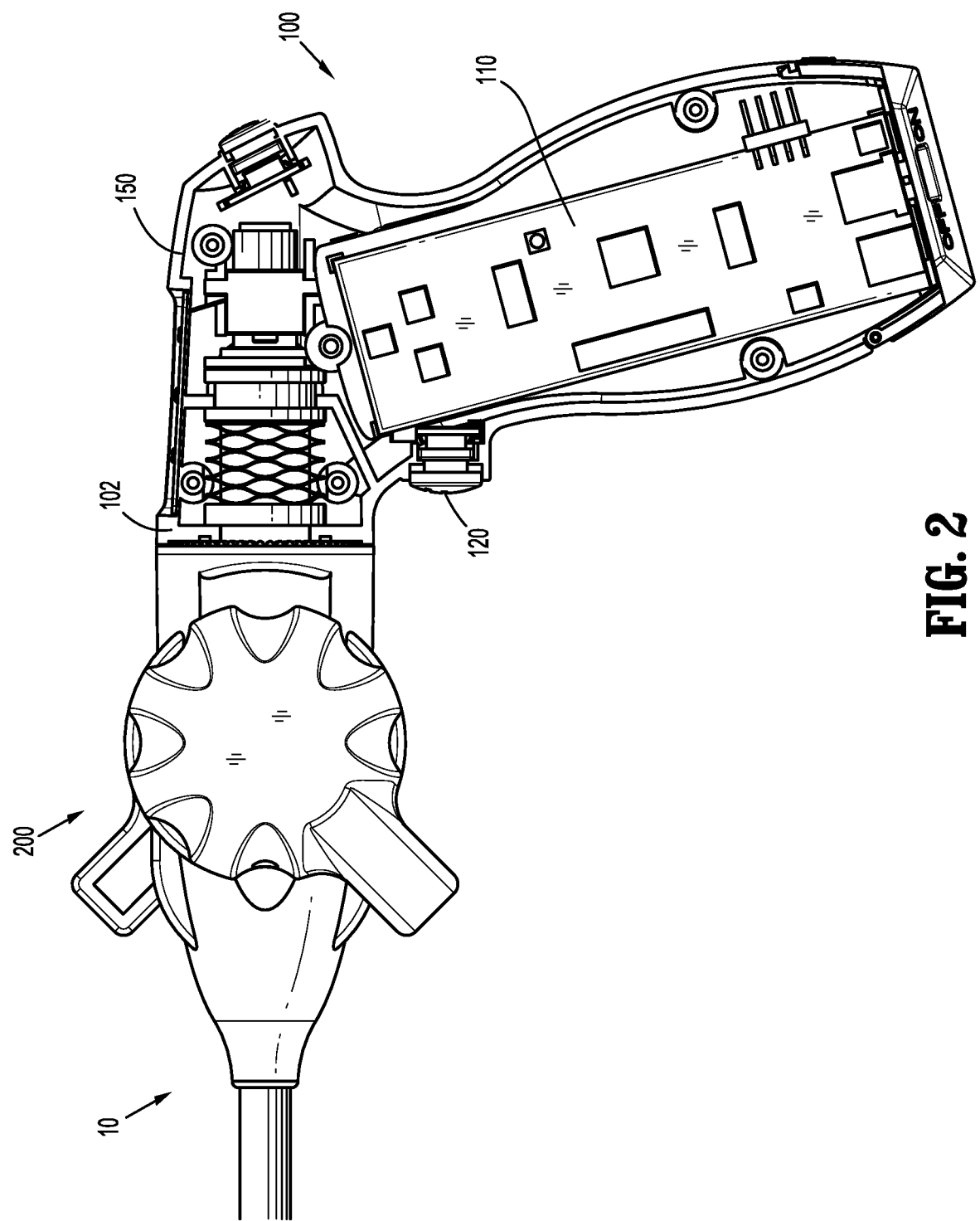
FIGS. 2 and 3 are side views of a first handle assembly with parts omitted for use with the surgical instrument of the present disclosure.
Figure 3:
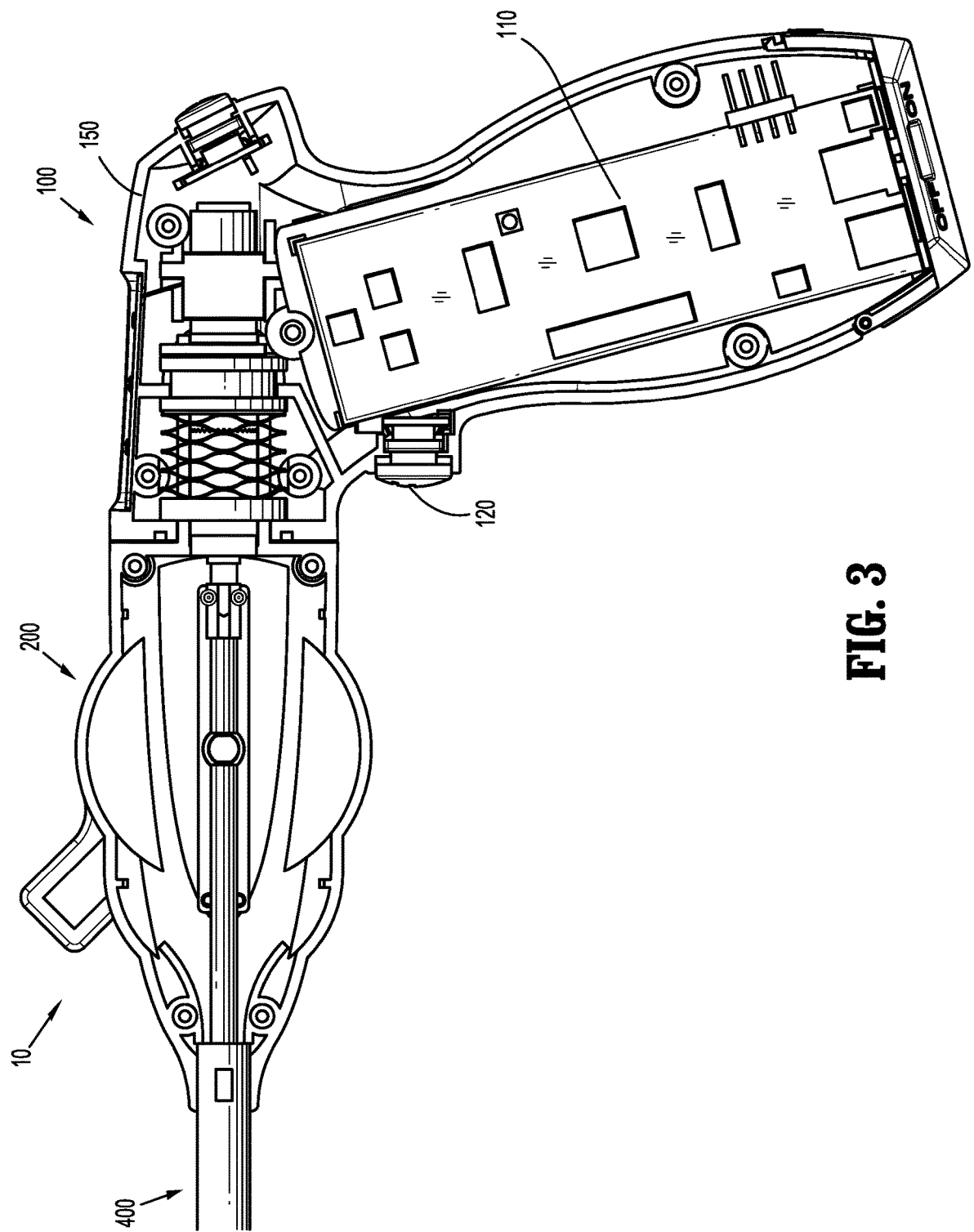
Figure 4:
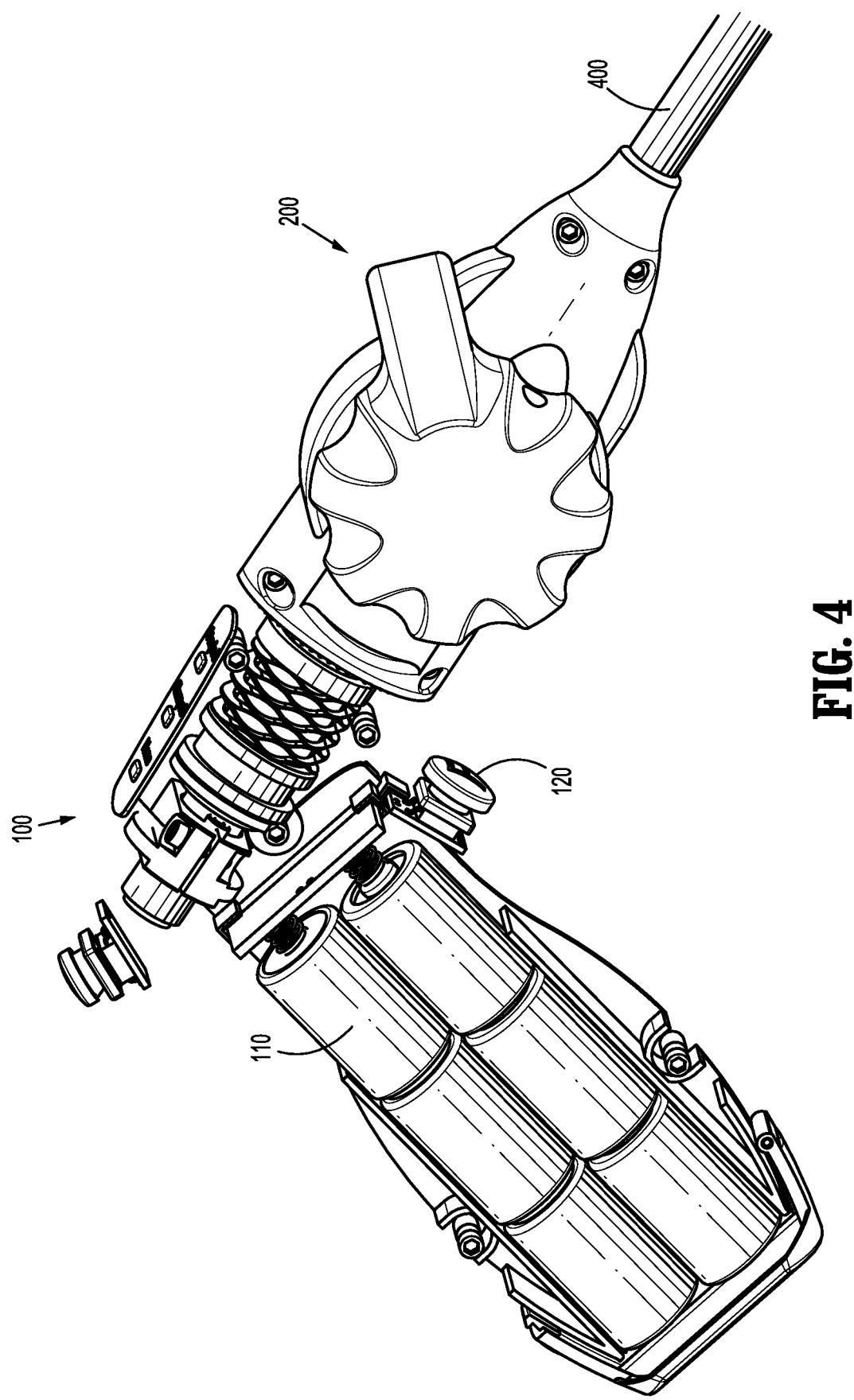
FIG. 4 is a perspective view of the first handle assembly in FIGS. 2 and 3 shown with parts omitted and partially disassembled.
Figure 5:
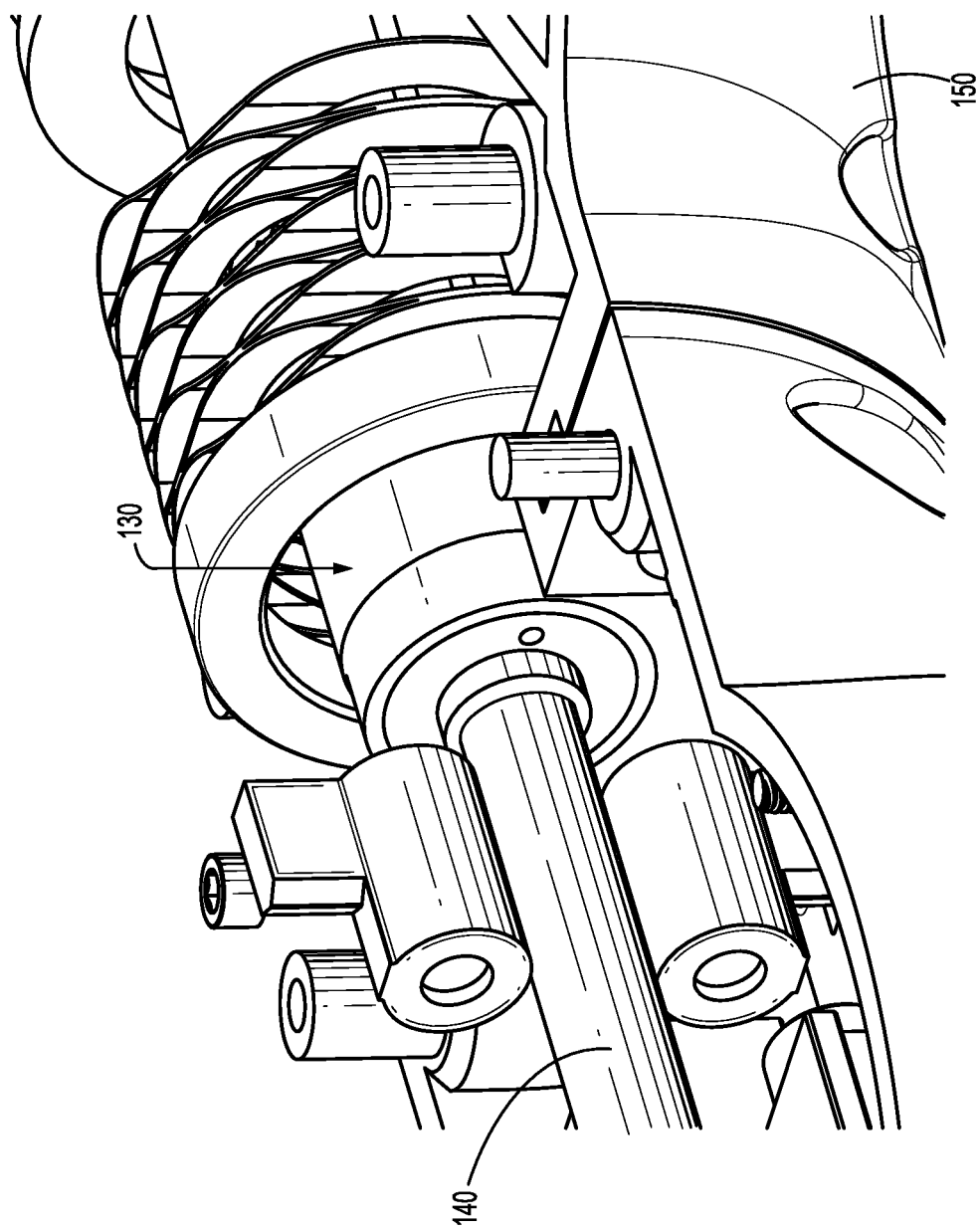
FIG. 5 is a perspective view of a portion of a drive assembly of the surgical instrument.
Figure 6:
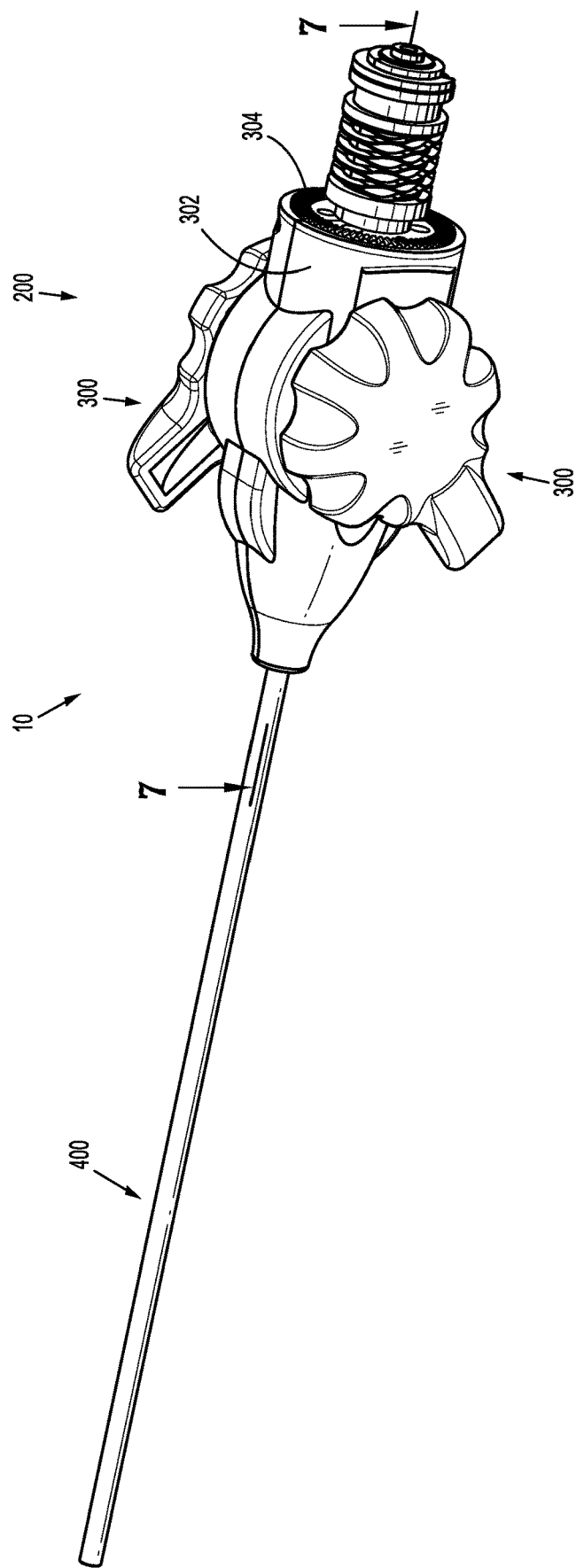
FIG. 6 is a perspective view of a portion of the surgical instrument with the handle assembly removed.
Figure 7:
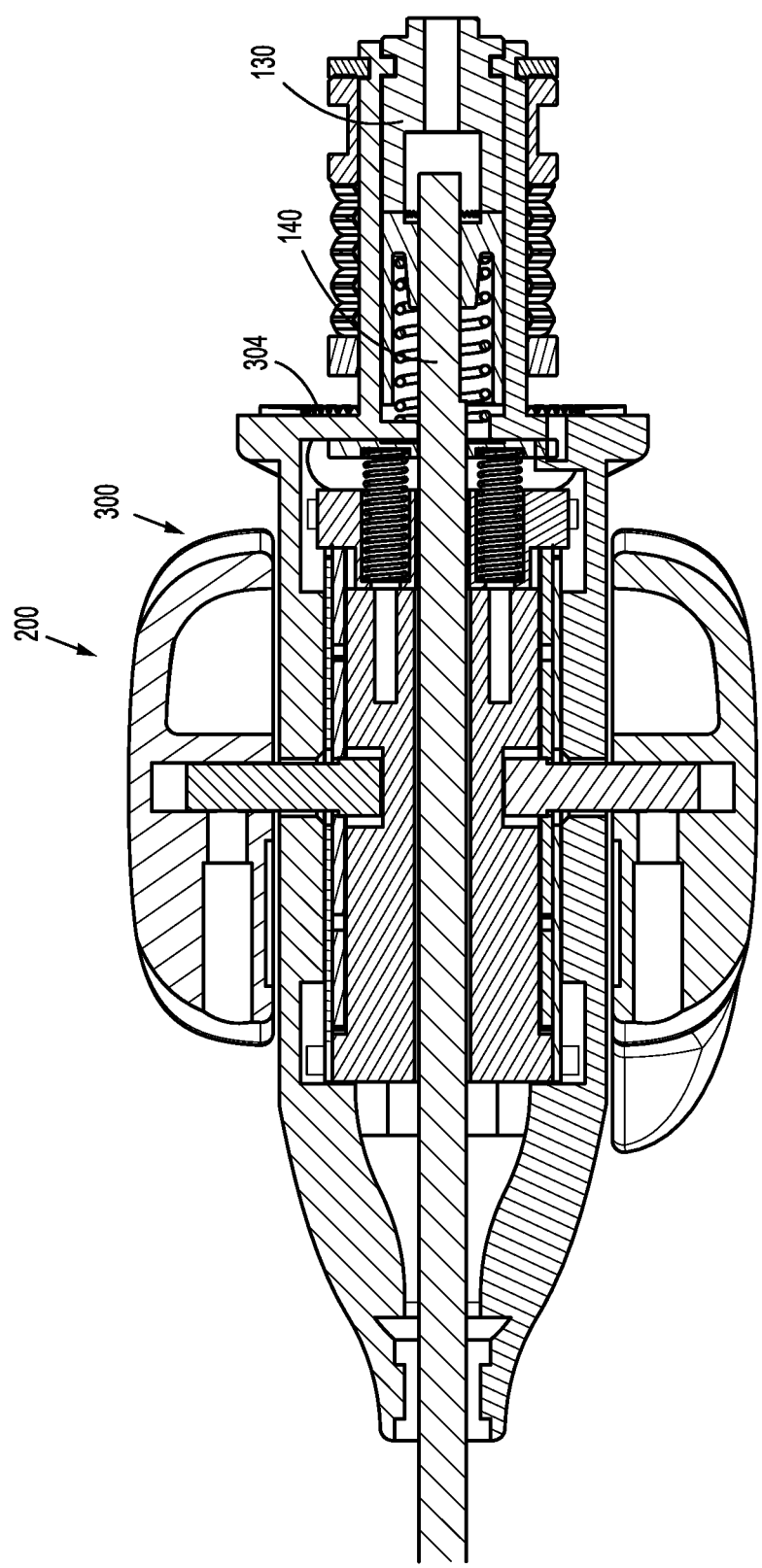
FIG. 7 is a longitudinal cross-sectional view of a control assembly of the surgical instrument taken along line 7-7 in FIG. 6.

Embodiments of the presently disclosed surgical systems, apparatuses and/or devices are described in detail with reference to the drawings, in which like reference numerals designate identical or corresponding elements in each of the several views. As used herein the term "distal" refers to portions of the system, apparatus and/or device, or component thereof, that are farther from the user, while the term "proximal" refers to portions of the system, apparatus and/or device, or component thereof, that are closer to the user.

Referring initially to FIG. 1, a hand-held, powered surgical instrument is shown and generally designated as reference number 10. Instrument 10 includes a first handle assembly 100, a control assembly 200, a shaft assembly 400 defining a longitudinal axis A-A, and an end effector 500. The end effector 500 is configured for actuation and manipulation by the first handle assembly 100 and the control assembly 200.

Referring now to FIGS. 1-8, further details of the instrument 10 are shown. The first handle assembly 100 is a powered handle assembly, which includes at least one battery 110 for providing power. The first handle assembly 100 also includes a trigger 120 (e.g., button or switch), which is disposed in electrical communication with the battery 110. First handle assembly 100 also includes a drive member 130 (e.g., a drive motor). Examples of drive motors that can be used with the instrument 10 of the present disclosure include brushless DC-micro motors with micro planetary gear heads such as those commercially available from The Faulhaber Group (Germany), and DC motors and planetary gear heads such as those commercially available from Maxon Motors (Germany).

Drive member 130 is disposed in electrical communication with the trigger 120 and is rotatable within a handle housing 150. A control rod 140 of instrument 10 is disposed in mechanical communication with drive member 130, and extends longitudinally through control assembly 200, through shaft assembly 400, and a distal portion of control rod 140 is disposed in mechanical communication with end effector 500. Generally, actuation of trigger 120 causes energy supplied by battery 110 to cause rotation of drive member 130 about longitudinal axis A-A. Rotation of drive member 130 causes longitudinal translation of control rod 140, which effectuates a function of end effector 500 (e.g., approximation of its jaws to clamp tissue, ejection of fasteners therefrom, and/or severing of tissue disposed between its jaw members). Further details of the features and functions of end effector 500 are disclosed in U.S. patent application Ser. No. 13/444,228, filed on Apr. 12, 2012, the entire disclosure of which is hereby incorporated by reference herein.

Figure 8:
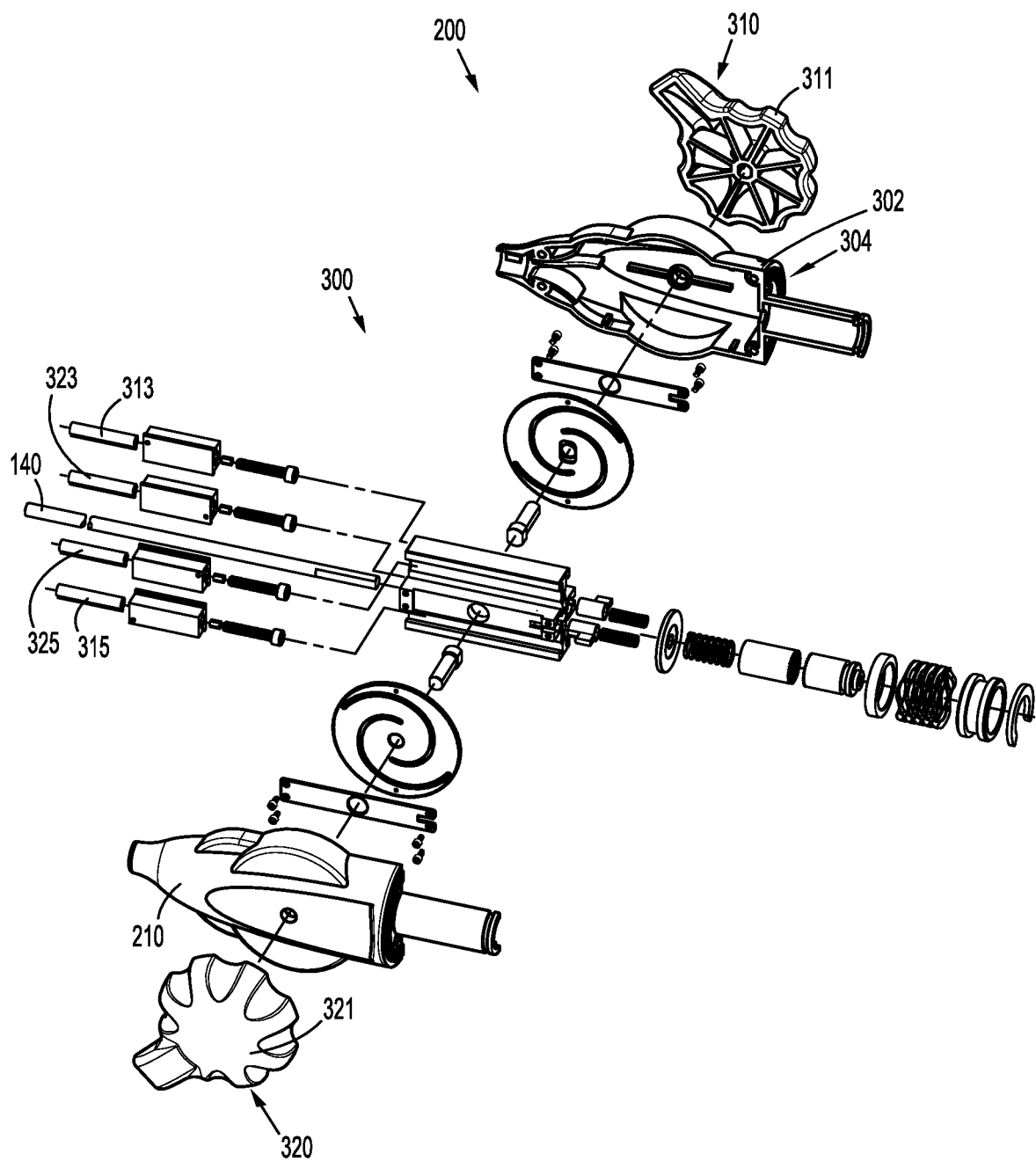
FIG. 8 is a perspective assembly view, with parts separated, of the control assembly of FIG. 7.
Figure 9:
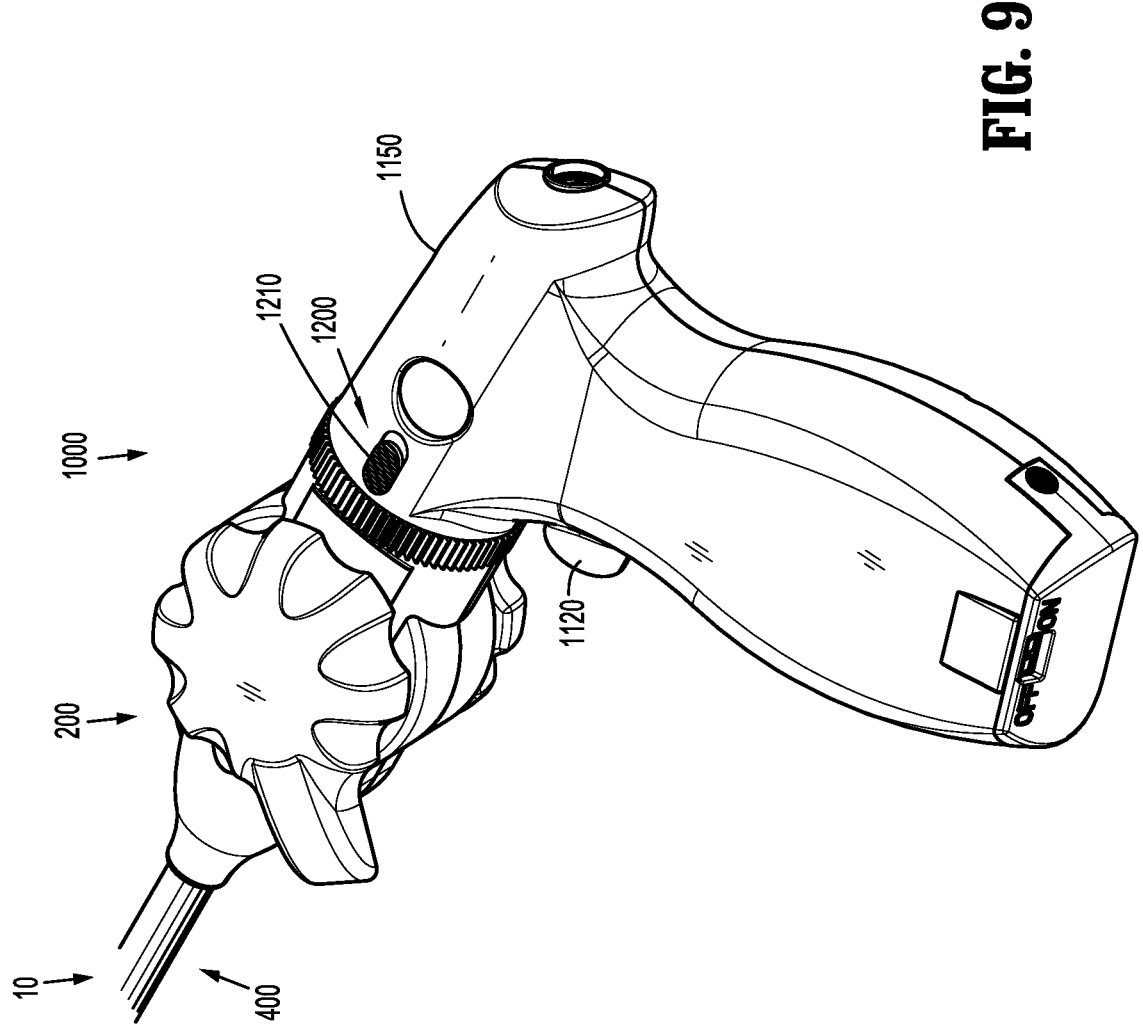
FIG. 9 is a perspective view of a second handle assembly engaged with the control assembly.

With particular reference to FIG. 8, an exploded view of the control assembly 200 is shown. Control assembly 200 includes an articulation assembly 300 and a rotation assembly 302. Articulation assembly 300 permits selective articulation of the end effector 500 to facilitate the manipulation and grasping of tissue. More particularly, two controls 310 and 320 include selectively rotatable wheels, dials or knobs, 311 and 321, respectively, that sit adjacent a control assembly housing 210. Each knob, e.g., knob 311, is independently moveable relative to the other knob, e.g., 321, and allows a user to selectively articulate the end effector 500 in a given plane of articulation relative to the longitudinal axis A-A. For example, rotation of knob 311 articulates end effector 500 along arrows "R" and "L" (FIG. 1; right-to-left articulation) by inducing a differential tension and a corresponding motion in steering cables 313 and 315. Similarly, rotation of knob 321 articulates end effector 500 along arrows "U" and "D" (FIG. 1; up-and-down articulation) by inducing a differential tension and a corresponding motion in steering cables 323 and 325. Further details of an articulation assembly are disclosed in U.S. patent application Ser. No. 13/543,931, which was filed on Jul. 9, 2012, the entire details of which are hereby incorporated by reference herein.

As mentioned above, control assembly 200 also includes a rotation assembly 302. Rotation assembly 302 includes control assembly housing 210, which is rotatable about the longitudinal axis A-A. It is further envisioned that control assembly housing 210 is rotatable about control rod 140. A distal portion of control assembly housing 210 is mechanically coupled to a proximal portion of shaft assembly 400, such that rotation of control assembly housing 210 causes a corresponding amount of rotation of shaft assembly 400 about the longitudinal axis A-A. Further, since end effector 500 is mechanically coupled to a distal portion of shaft assembly 400, rotation of shaft assembly 400 results in rotation of end effector 500 about longitudinal axis A-A. Additionally, it is envisioned that engagement structure 304 adjacent a proximal portion of control assembly housing 210 mechanically engages engagement structure 102 (FIG. 2) adjacent a distal portion of first handle assembly 100 facilitate the rotational relationship therebetween. Thus, in disclosed embodiments, instrument 10 includes a powered direct drive system with manual steering.

With reference to FIGS. 9-14, a second handle assembly 1000 is shown. Second handle assembly 1000 is configured to quickly allow a user to separate second handle assembly 1000 from the surgical instrument 10, e.g., control assembly 200. Second handle assembly 1000 is a powered handle assembly and includes at least one battery (not explicitly shown in the accompanying figures; it is envisioned that the at least one battery is similar to the at least one battery 110 of first handle assembly 100) for providing power. The second handle assembly 1000 also includes a trigger 1120 (e.g. button or switch), which is disposed in electrical communication with the battery. A drive member 1130 of second handle assembly 1000 is disposed in electrical communication with the trigger 1120 and is rotatable within a handle housing 1150. When second handle assembly 1000 is engaged with control assembly 200 and shaft assembly 400, drive member 1130 is disposed in mechanical cooperation with control rod 140 of surgical instrument 10. Here, actuation of trigger 1120 causes energy supplied by the battery to cause rotation of drive member 1130 about longitudinal axis A-A. Rotation of drive member 1130 causes longitudinal translation of control rod 140, which effectuates a function of end effector 500.

Figure 10:
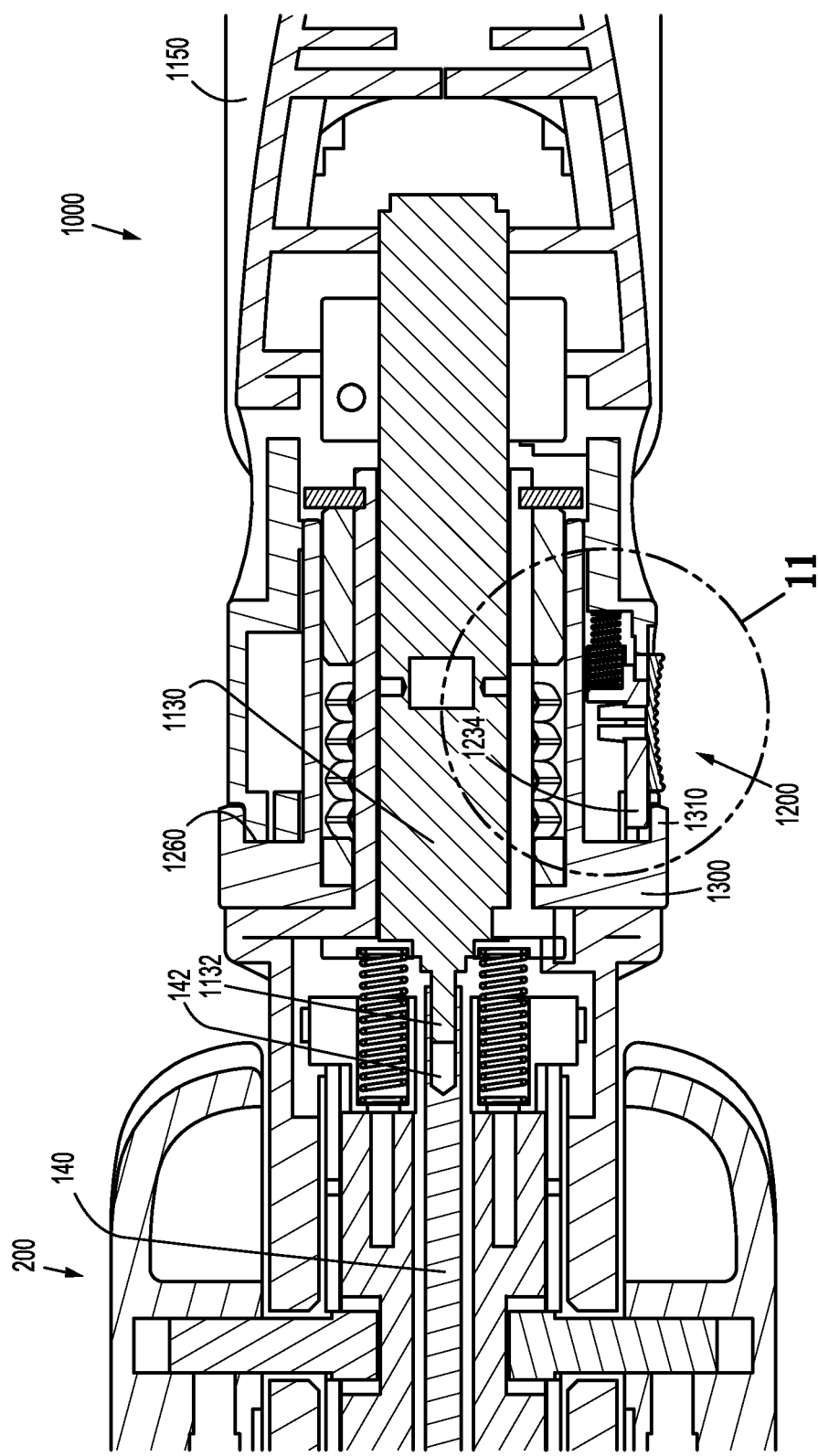
FIG. 10 is a longitudinal cross-sectional view of the second handle assembly engaged with the control assembly.
Figure 11:
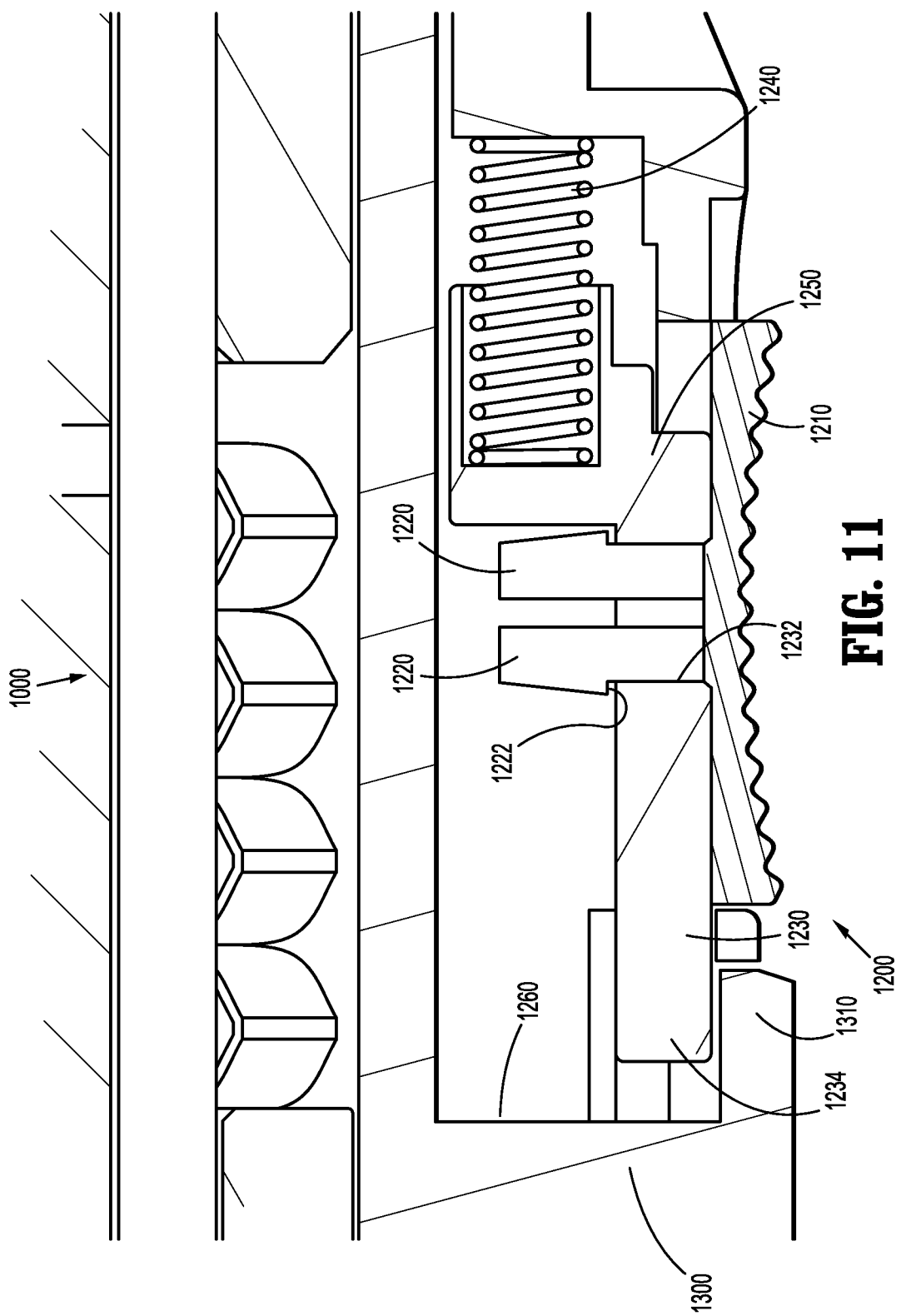
FIG. 11 illustrates the area of detail indicated in FIG. 10.
Figure 14:
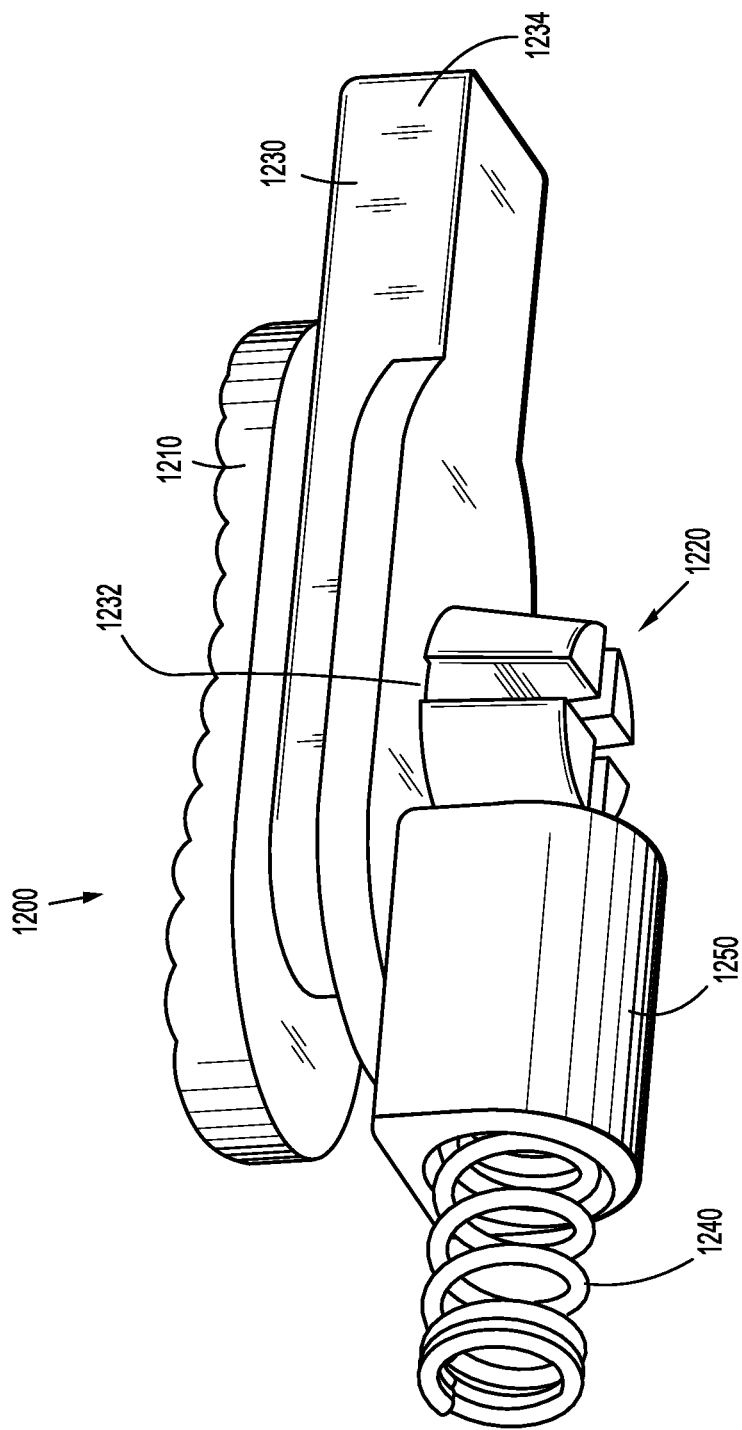
FIG. 14 is a perspective view of a safety assembly of the second handle assembly.

With specific reference to FIGS. 10, 11 and 14, second handle assembly 1000 also includes a spring loaded lock/release mechanism 1200 for facilitating attachment to and detachment from surgical instrument 10 (e.g., control assembly 200). With particular reference to FIGS. 11 and 14, spring loaded lock/release mechanism 1200 includes a user-actuatable switch 1210, a plurality of fingers 1220, a plate 1230, a biasing element 1240, and a housing 1250. Fingers 1220 depend from switch 1210 and extend through an aperture 1232 in plate 1230. The spacing between fingers 1220 allows approximation/deflection therebetween, and facilitates assembly between switch 1210 and plate 1230. As can be appreciated, lips 1222 on fingers 1220 help secure fingers 1220 and switch 1210 to plate 1230. Housing 1250 is secured to plate 1230 and is configured to house at least a portion of biasing element 1240.

Figure 13:
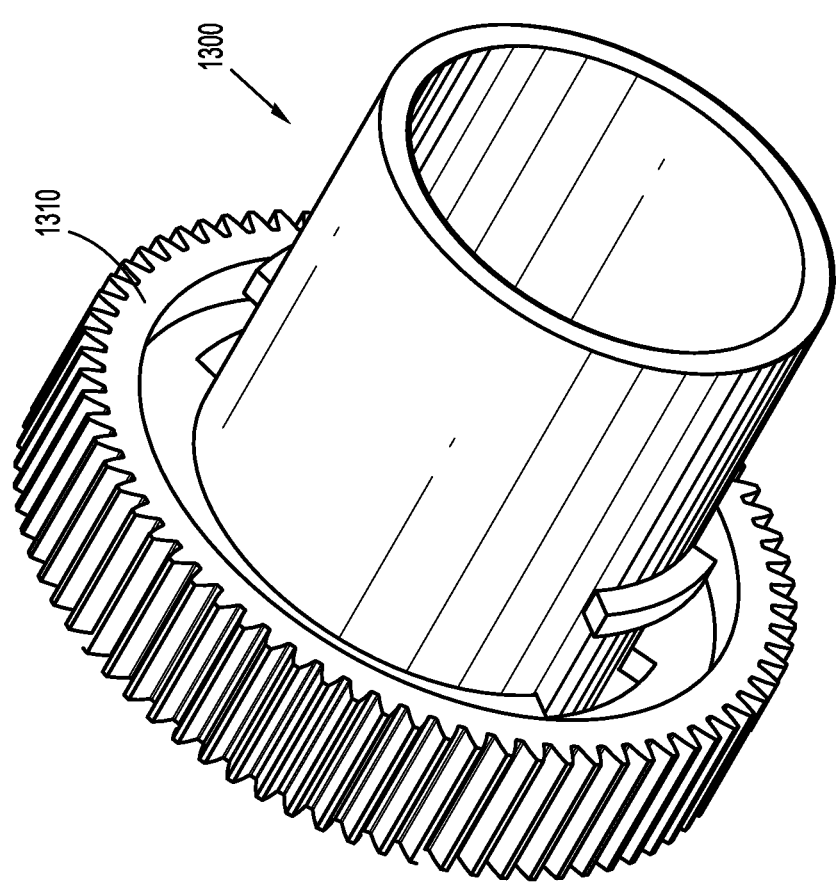
FIG. 13 is a perspective view of a sleeve of the second handle assembly.

When second handle assembly 1000 is engaged with surgical instrument 10, in particular control assembly 200, biasing element 1240 urges housing 1250 and plate 1230 distally towards control assembly 200. This distal biasing causes a distal portion 1234 of plate 1230 to extend within a lip 1310 of a sleeve 1300 of control assembly 200. A perspective view of sleeve 1300, which extends proximally from control assembly 200, is shown in FIG. 13. Further, a distal face 1260 of second handle assembly 1000 is configured to mechanically engage sleeve 1300, e.g., radially within lip 1310, to help further secure the engagement between second handle assembly 1000 and control assembly 200. The mechanical engagement between plate 1230 and control assembly 200 (e.g., sleeve 1300 of control assembly 200), and the mechanical engagement between distal face 1260 and surgical instrument 10 (e.g., sleeve 1300) help maintain engagement between second handle assembly 1000 and control assembly 200 of surgical instrument 10.

Figure 12:
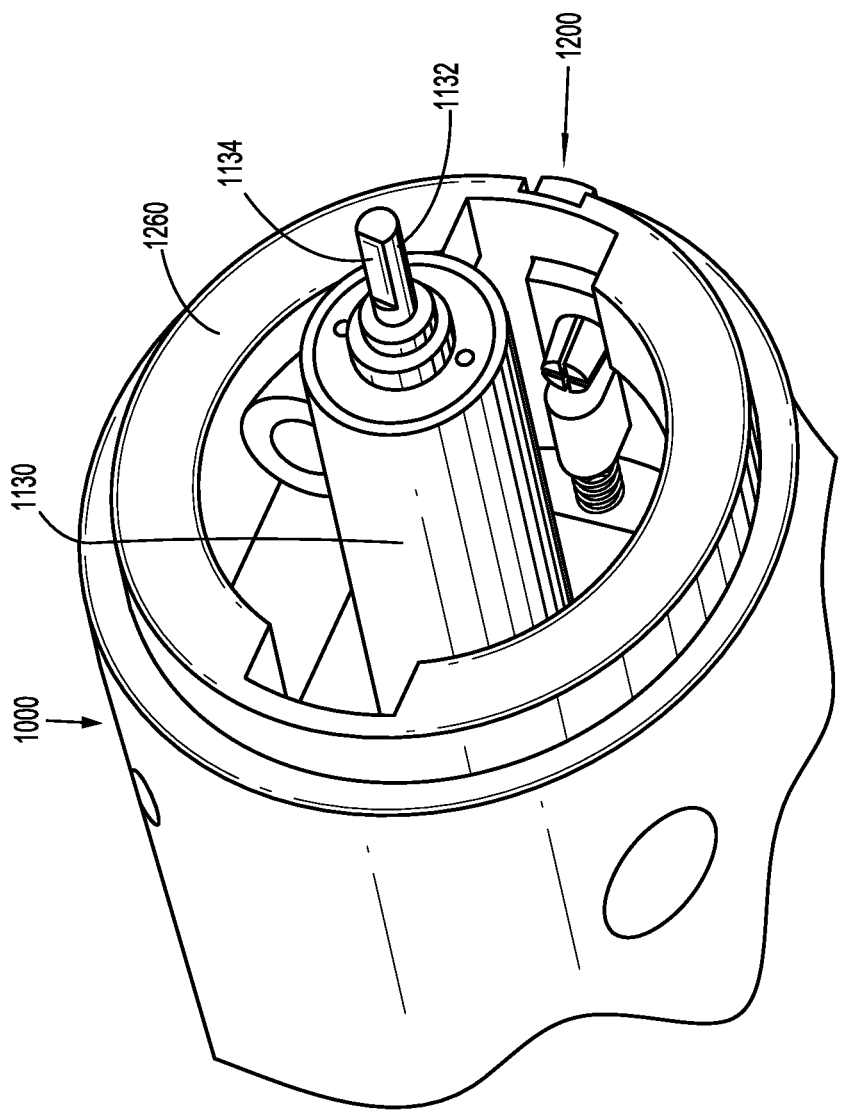
FIG. 12 is a perspective view looking into the second handle assembly.

As discussed above, when second handle assembly 1000 is mechanically engaged with control assembly 200 of surgical instrument 10, drive member 1130 is aligned and disposed in mechanical cooperation with control rod 140 of surgical instrument 10. Here, actuation of trigger 1120 causes energy supplied by the battery 110 to cause rotation of drive member 1130 about longitudinal axis A-A, which causes distal translation of control rod 140. As shown in FIG. 12, a distal end of drive member 1130 includes a pin 1132. Pin 1132 includes a generally circular cross-section, which includes a flat surface 1134. When second handle assembly 1000 is mechanically engaged with control assembly 200 of surgical instrument 10, pin 1132 engages a cavity 142 of control rod 140 (see FIG. 10). A cross-section of cavity 142 is complementarily- or similarly-shaped to the cross-section of pin 1132, such that flat surface 1134 of pin 1132 engages a corresponding flat surface of cavity 142 to limit or prevent rotation therebetween.

If desired, a user is able to remove or disconnect second handle assembly 1000 from surgical instrument 10 (e.g., prior to a surgical procedure, during a surgical procedure, or after a surgical procedure). To remove second handle assembly 1000 from control assembly 200 of surgical instrument 10, a user moves switch 1210 of spring loaded lock/release mechanism 1200 proximally against the bias of biasing element 1240. A predetermined amount of proximal movement of switch 1210 causes distal portion 1234 of plate 1230 to move out of engagement with lip 1310 of sleeve 1300. Once plate 1230 is disengaged from sleeve 1300, a user is able to remove or disconnect second handle assembly 1000 from control assembly 200 of surgical instrument 10, e.g., by titling second handle assembly 1000 and moving second handle assembly 1000 proximally with respect to control assembly 200 of surgical instrument 10.

Referring now to FIGS. 15-29, a third handle assembly 2000 is shown. Third handle assembly 2000 is a manually operable handle assembly (i.e., a manual drive system that does not include a power source), and is also mechanically engageable with control assembly 200 of surgical instrument 10. It is envisioned that a user (e.g., surgeon) is able to replace second handle assembly 1000 with third handle assembly 2000 at any time, including during a surgical procedure (e.g., due to a battery failure, battery disruption, electrical or mechanical failure). It is envisioned that third handle assembly 2000 is usable with surgical instrument 10 on its own, or with an additional housing assembly or enclosure 2010 (a portion of housing assembly 2010 is shown in FIGS. 25-29).

Generally, third handle assembly 2000 includes an actuation assembly 2100, a housing assembly 2200, a rotatable rod 2300, a switch assembly 2400, a first gear assembly 2500, and a second gear assembly 2600. Actuation of a movable handle or lever 2110 of actuation assembly 2100 causes rotation of first gear assembly 2500 or second gear assembly 2600, which causes rotation of rotatable rod 2300 in a first or second direction, respectively. When engaged with or to control assembly 200 of surgical instrument 10, rotation of rotatable rod 2300 effects a function of the end effector 500, as discussed above. It is envisioned that rotation of rotatable rod 2300 in a first direction effects a first function of end effector 500 (e.g., distal translation of a clamping member to approximate the jaws), and that rotation of rotatable rod 2300 in a second direction effects a second function of end effector 500 (e.g., proximal translation of the clamping member to open the jaws).

Figure 24:
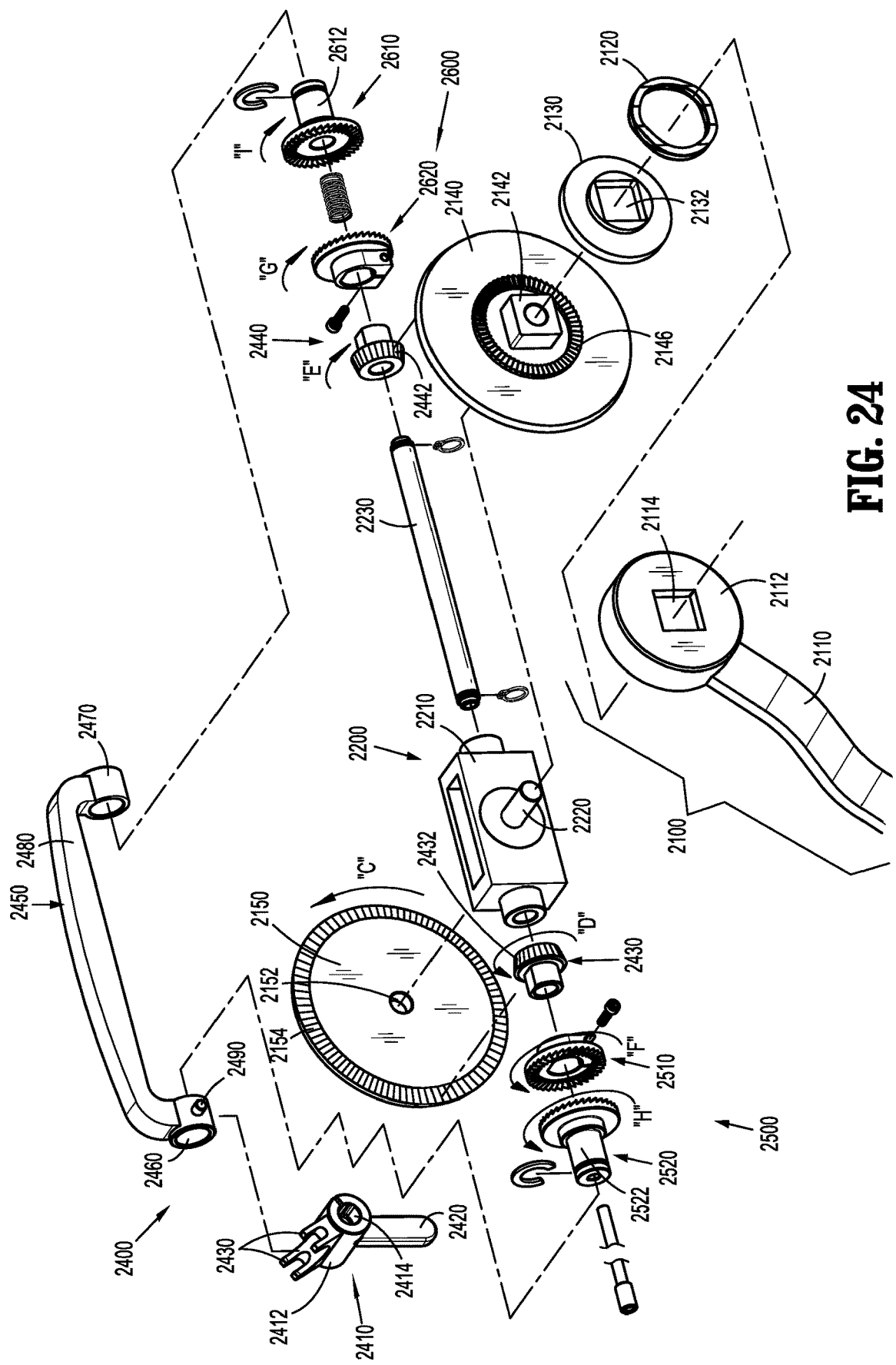
FIG. 24 is a perspective, assembly view, with parts separated, of a portion of the third handle assembly.
Figure 25:
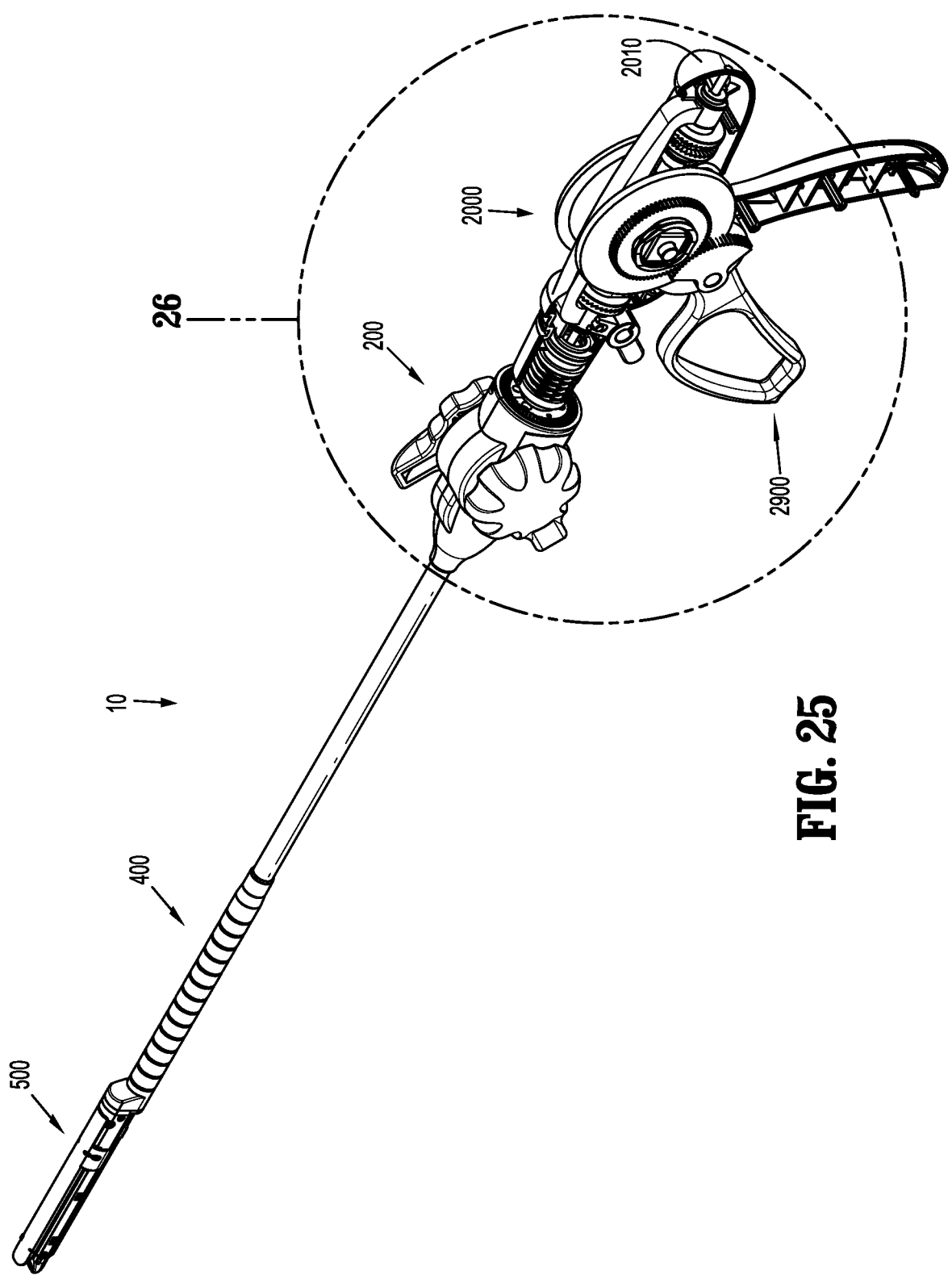
FIG. 25 is a perspective view of the third handle assembly engaged with the surgical instrument and a handle housing.
Figure 26:
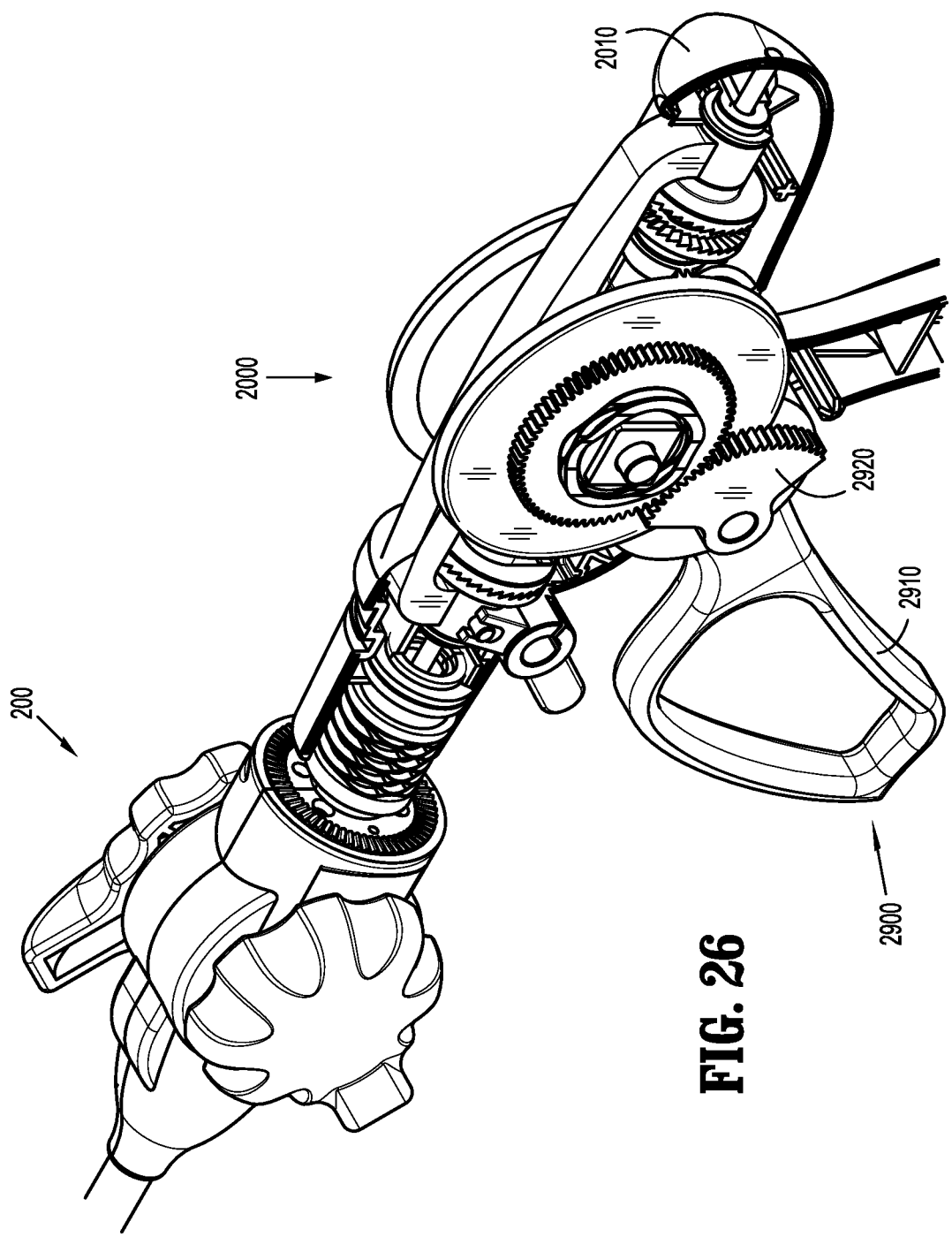
FIG. 26 illustrates the area of detail indicated in FIG. 25.
Figure 27:
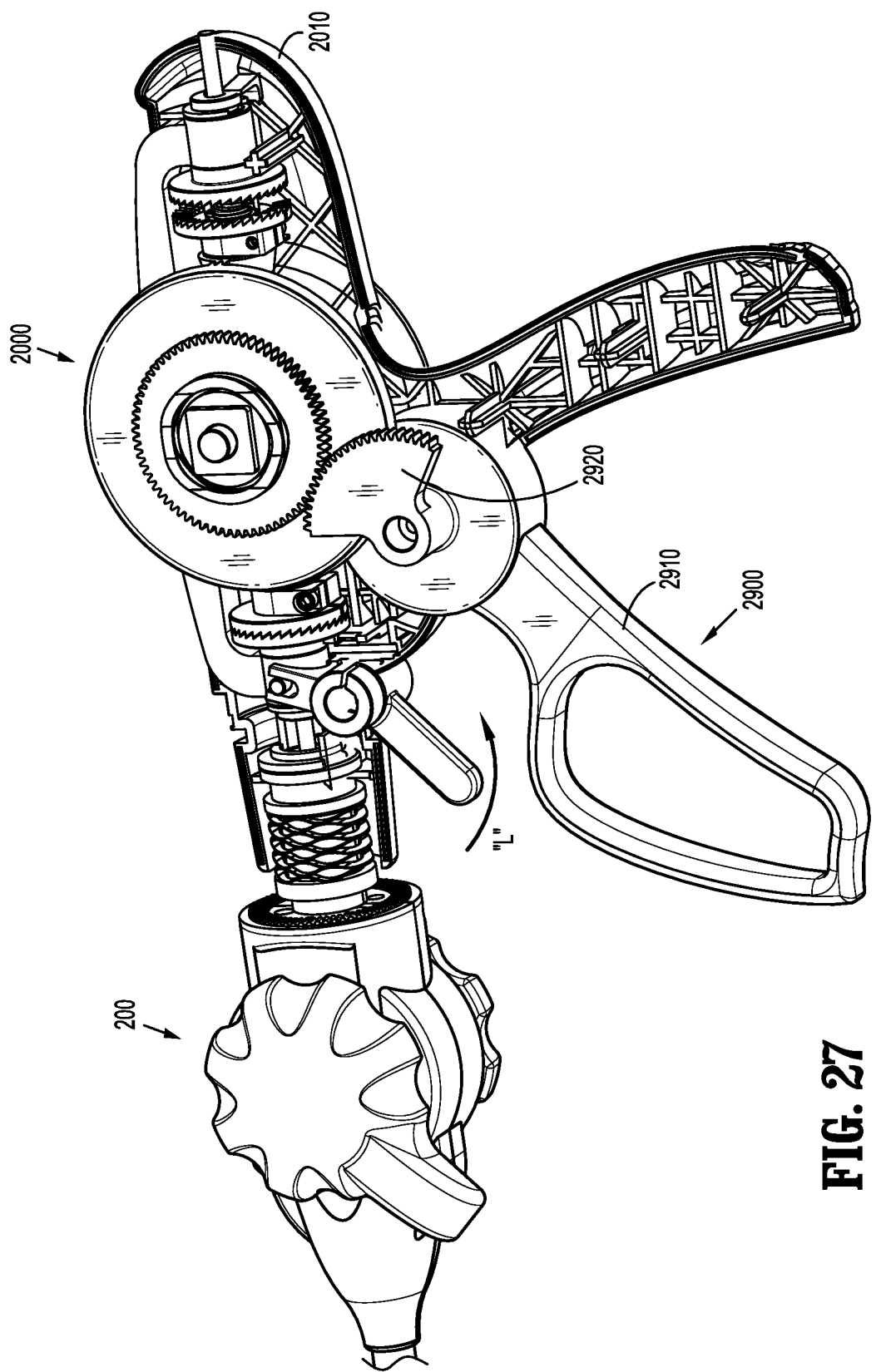
FIGS. 27 and 28 are perspective views of the third handle assembly, with parts removed, illustrated in engagement with the control assembly and the handle housing.
Figure 28:
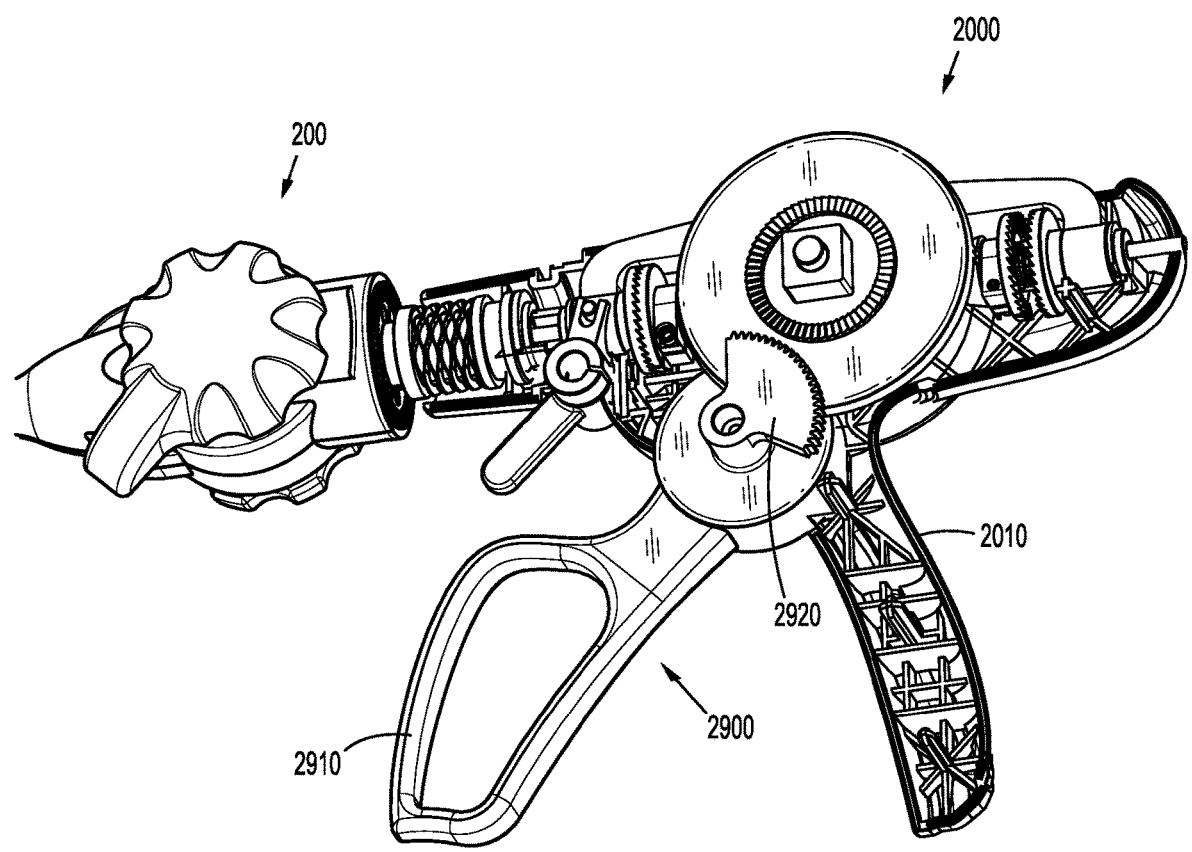

More particularly, and with specific reference to FIG. 24, actuation assembly 2100 includes movable handle or lever 2110, a wave spring 2120, a spacer 2130, a first gear 2140, and a second gear 2150. Housing assembly 2200 includes a housing block 2210, an axle 2220, and a tubular member 2230. Switch assembly 2400 includes a hand switch 2410, and a switch bar 2450. First gear assembly 2500 includes a first proximal gear 2510 and a first distal gear 2520. Second gear assembly 2600 includes a second proximal gear 2610 and a second distal gear 2620.

Figure 23:
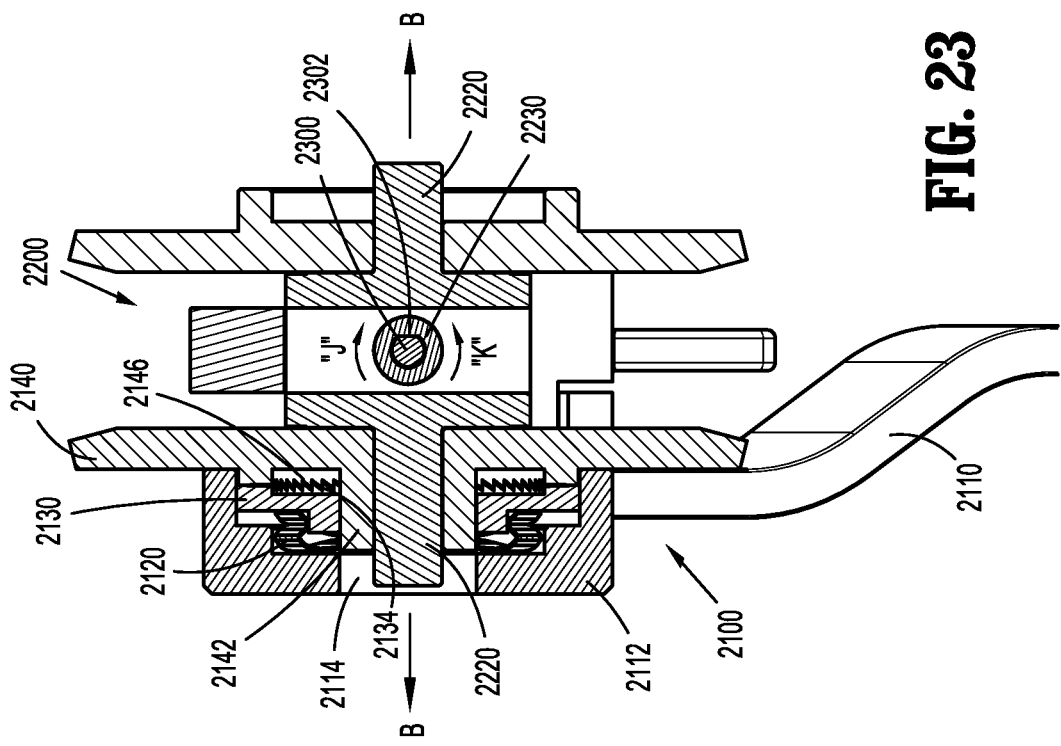
FIG. 23 is a cross-sectional view of a portion of the third handle assembly taken along line 23-23 of FIG. 18.

With reference to FIGS. 23 and 24, first gear 2140 of actuation assembly 2100 includes a non-circular protrusion 2142 extending laterally therefrom, which supports spacer 2130 and wave spring 2120. As shown, spacer 2130 includes a non-circular aperture 2132 extending therethrough, which is the same or complimentary shape (illustrated as a square, but other non-circular shapes are contemplated) as protrusion 2142 of first gear 2140. As can be appreciated, the non-circular shapes of aperture 2132 and protrusion 2142 limit or prevent rotation between spacer 2130 and first gear 2140 (e.g., spacer 2130 and first gear 2140 are keyed to one another). Further, and with particular reference to FIG. 23, spacer 2130 includes a set of teeth 2134 thereon, which are configured and dimensioned to mesh with a set of teeth 2146 of first gear 2140. It is envisioned that teeth 2134 of spacer 2130 and teeth 2146 of first gear 2140 form a one-way clutch to help ensure repeating motion of the trigger.

Additionally, movable handle or lever 2110 includes a housing or head portion 2112 that is configured to house at least a portion of wave spring 2120 and spacer 2130, and which is dimensioned for a snap-fit engagement with first gear 2140. Wave spring 2120 helps ensure proper and consistent engagement between set of teeth 2134 of spacer 2130 and set of teeth 2146 of first gear 2140. Further, housing or head portion 2112 of movable handle or lever 2110 includes a non-circular aperture 2114 that is configured and dimensioned to be supported by and keyed to protrusion 2144 of first gear 2140, thus limiting or preventing rotation therebetween. Accordingly, rotation of movable handle or lever 2110 results in corresponding rotation of first gear 2140 and, as discussed in further detail below, rotation of first gear 2140 results in corresponding rotation of second gear 2150.

With continued reference to FIGS. 23 and 24, actuation assembly 2100 is pivotably mounted to housing block 2210. Specifically, an aperture 2144 of first gear 2140 is positioned on axle 2220 of housing block 2210, and an aperture 2152 of second gear 2150 is also positioned on axle 2220. Further, first gear 2140 and second gear 2150 are non-rotationally supported by axle 2220, e.g., pinned or keyed to axle 2220. That is, first gear 2140 and second gear 2150 cannot rotate with respect to axle 2220. Axle 2220, in turn, is rotatably supported by housing block 2210, which enables rotation between axle 2220 and housing block 2210, and thus allows rotation between first gear 2140 and second gear 2150 with respect to housing block 2210. Further, rotation of first gear 2140 causes rotation of axle 2220, which causes rotation of second gear 2150.

Figure 21:
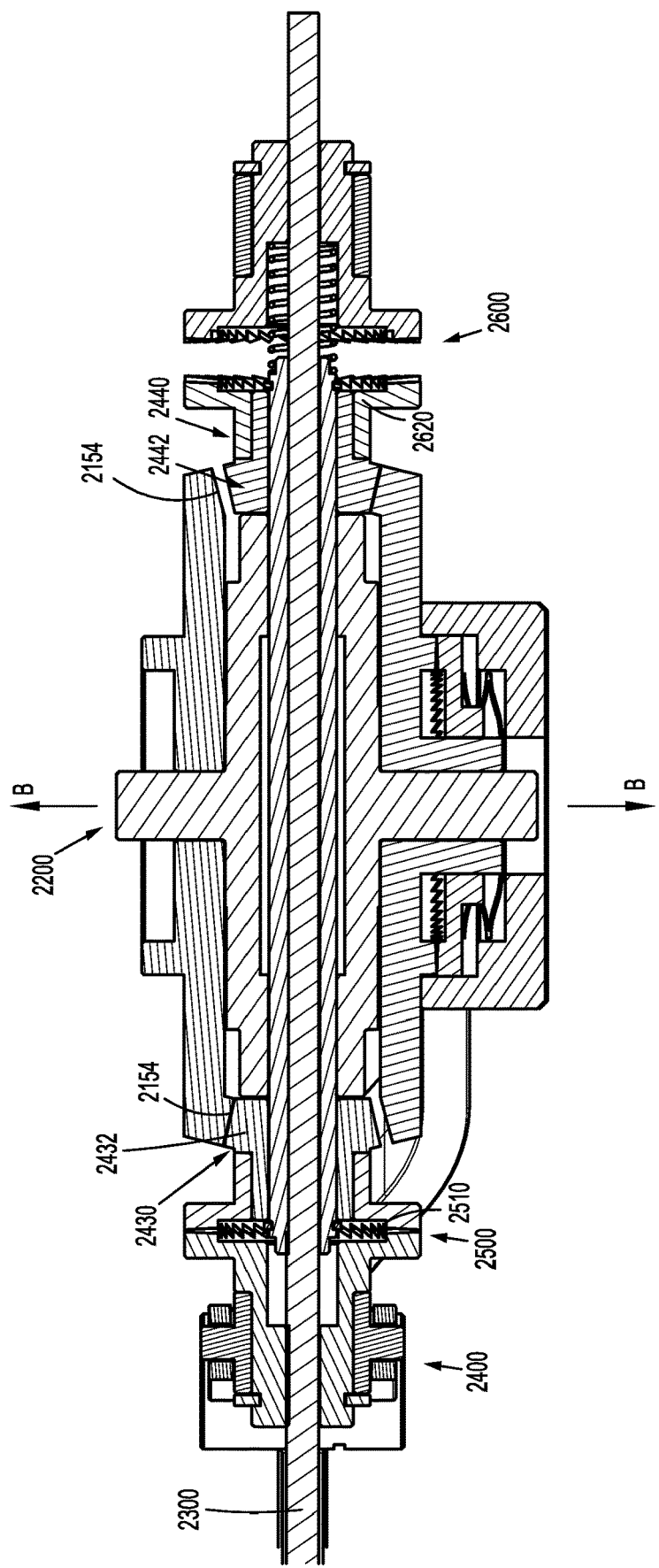
FIG. 21 is a longitudinal cross-sectional view of the third handle assembly taken along line 21-21 of FIG. 20.

With reference to FIGS. 21 and 24, rotation of second gear 2150 causes rotation of both a distal bevel gear 2430 and a proximal bevel gear 2440. Further, rotation of second gear 2150 results in teeth 2154 of second gear 2150 engaging teeth 2432 of distal bevel gear 2430, and also results in teeth 2154 of second gear 2150 engaging teeth 2442 of proximal bevel gear 2440. As shown, second gear 2150 is rotatable about axis B-B defined by axle 2220 (FIGS. 21 and 23), which is offset 90° from axis A-A, about which distal bevel gear 2430 and proximal bevel gear 2440 are rotatable. Distal bevel gear 2430 is rotationally fixed (e.g., pinned) to first proximal gear 2510 of first gear assembly 2500, such that, rotation of distal bevel gear 2430 causes a corresponding rotation of first proximal gear 2510. Similarly, proximal bevel gear 2440 is rotationally fixed (e.g., pinned or keyed) to second distal gear 2620 of second gear assembly 2600, such that, rotation of proximal bevel gear 2440 causes a corresponding rotation of second distal gear 2620. Accordingly, actuation of movable handle or lever 2110 in the substantial direction of arrow "A" (FIG. 15) results in rotation of first gear 2140 in the substantial direction of arrow "B" (FIG. 15), and rotation of second gear 2150 in the substantial direction of arrow "C" (FIGS. 15 and 24; as shown, arrows "A," "B," and "C" are in the same general counter-clockwise direction). Further, rotation of second gear 2150 causes rotation of distal bevel gear 2430 in the substantial direction of arrow "D" (FIG. 24) and causes rotation of proximal bevel gear 2440 in the substantial direction of arrow "E" (FIG. 24). As shown, arrows "D" and "E" are in the opposite direction from each other. Moreover, rotation of distal bevel gear 2430 in the substantial direction of arrow "D" causes corresponding rotation of first proximal gear 2510 in the substantial direction of arrow "F" (which is the same general direction as arrow "D"). Similarly, rotation of proximal bevel gear 2440 in the substantial direction of arrow "E" causes corresponding rotation of second distal gear 2620 in the substantial direction of arrow "G" (which is the same general direction of arrow "E").

When first proximal gear 2510 is mechanically engaged with first distal gear 2520 (as discussed below), rotation of first proximal gear 2510 in the substantial direction of arrow "F" causes rotation of first distal gear 2520 in the substantial direction of arrow "H" (FIG. 24; as shown, arrows "D" and "F" are in the same general direction as each other; the direction of arrows "D" and "F" is generally clockwise when looking distally from a proximal end of third handle assembly 2000). When second distal gear 2620 is mechanically engaged with second proximal gear 2610 (as discussed below), rotation of second distal gear 2620 in the substantial direction of arrow "G" causes rotation of second proximal gear 2610 in the substantial direction of arrow "I" (FIG. 24).

Figure 22:
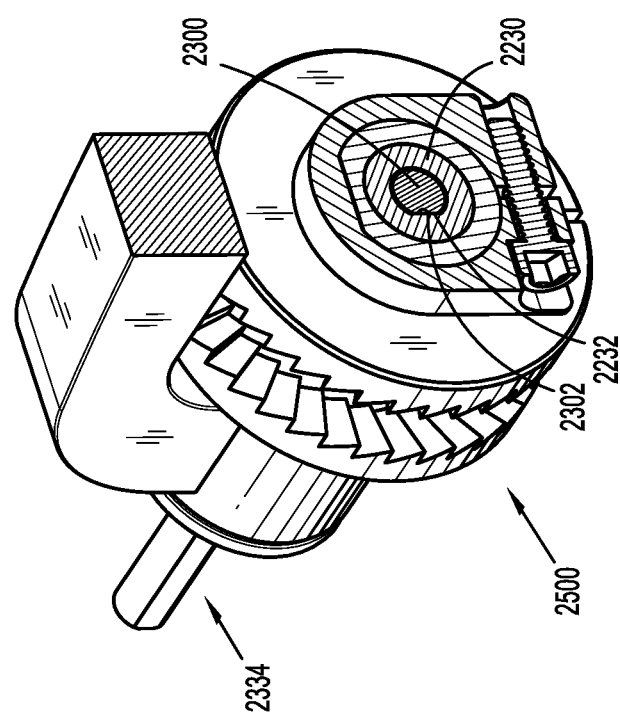
FIG. 22 is a cut-away perspective view of a portion of the third handle assembly taken along line 22-22 of FIG. 20.

Both first distal gear 2520 and second proximal gear 2610 are rotationally and longitudinally fixed with respect to rotatable rod 2300. As shown in FIGS. 22 and 23, rotatable rod 2300 has a radial cross-section including a flat surface 2302, which engages a flat surface 2232 of tubular member 2230 to limit or prevent rotation therebetween. Thus, rotation of first distal gear 2520 in the substantial direction of arrow "H" causes corresponding rotation of rotatable rod 2300 in the substantial direction of arrow "J" (shown as clockwise in FIG. 23). Rotation of second proximal gear 2610 in the substantial direction of arrow "I" causes corresponding rotation of rotatable rod 2300 in the substantial direction of arrow "K" (shown in counter-clockwise in FIG. 23). It is also envisioned that each of distal bevel gear 2430, proximal bevel gear 2440, first proximal gear 2510, first distal gear 2520, second proximal gear 2610 and second distal gear 2620 also includes a corresponding flat surface to limit or prevent rotation with respect to rotatable rod 2300.

Additionally, a distal portion 2334 of rotatable rod 2300 is configured for mechanical engagement with cavity 142 of control rod 140 of surgical instrument. As can be appreciated, rotation of rotatable rod 2300 results in a corresponding rotation of control rod 140. Thus, when rotatable rod 2330 rotates in a first direction, control rod 140 rotates in the first direction, and when rotatable rod 2330 rotates in a second direction, control rod 140 rotates in the second direction. Further, as discussed above, it is envisioned that rotation of control 140 in a first direction effects a first function of end effector 500 (e.g., approximating the jaw members) and rotation of control rod 140 in a second direction effects a second function of end effector 500 (e.g., opening the jaw members).

Figure 15:
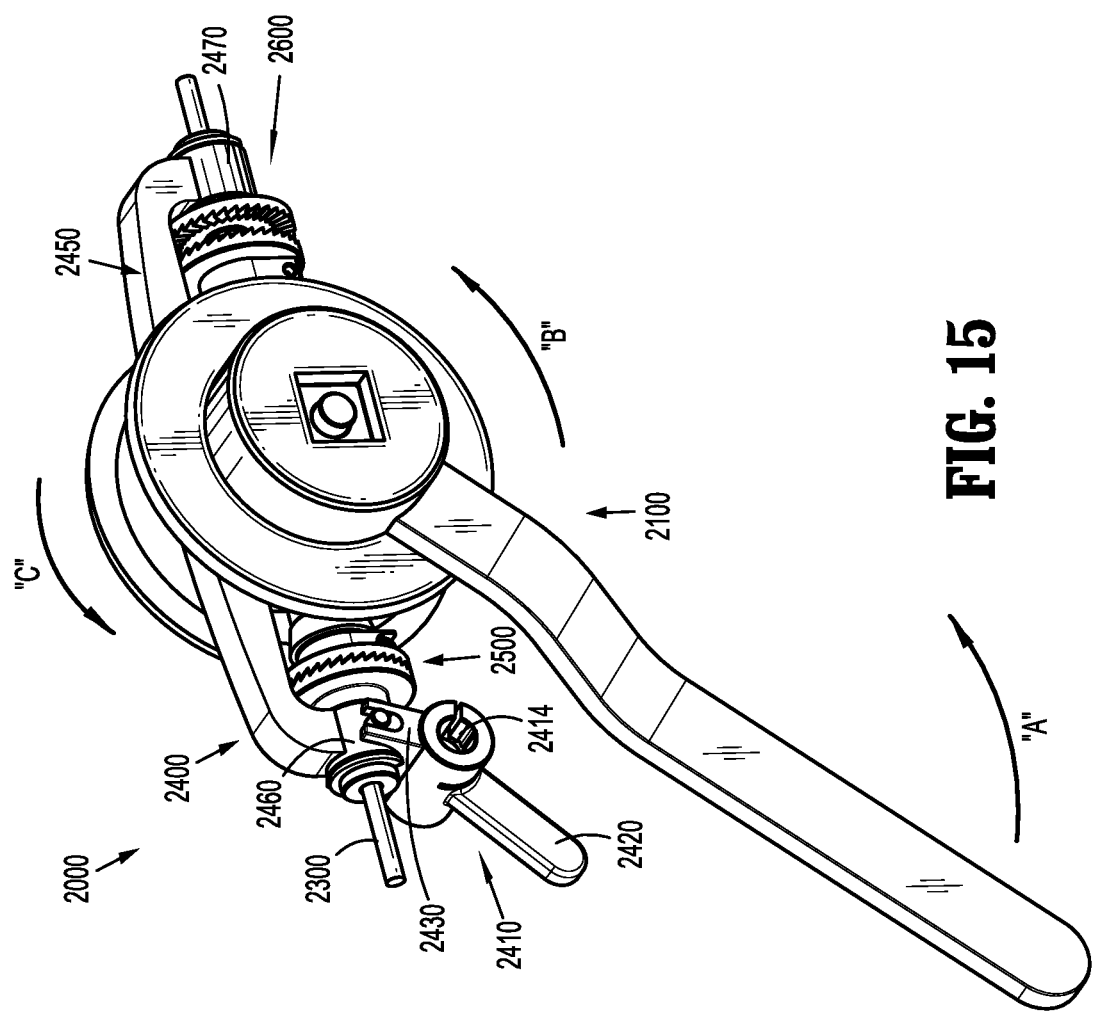
FIGS. 15-17 are perspective views of a third handle assembly for use with the surgical instrument.
Figure 16:
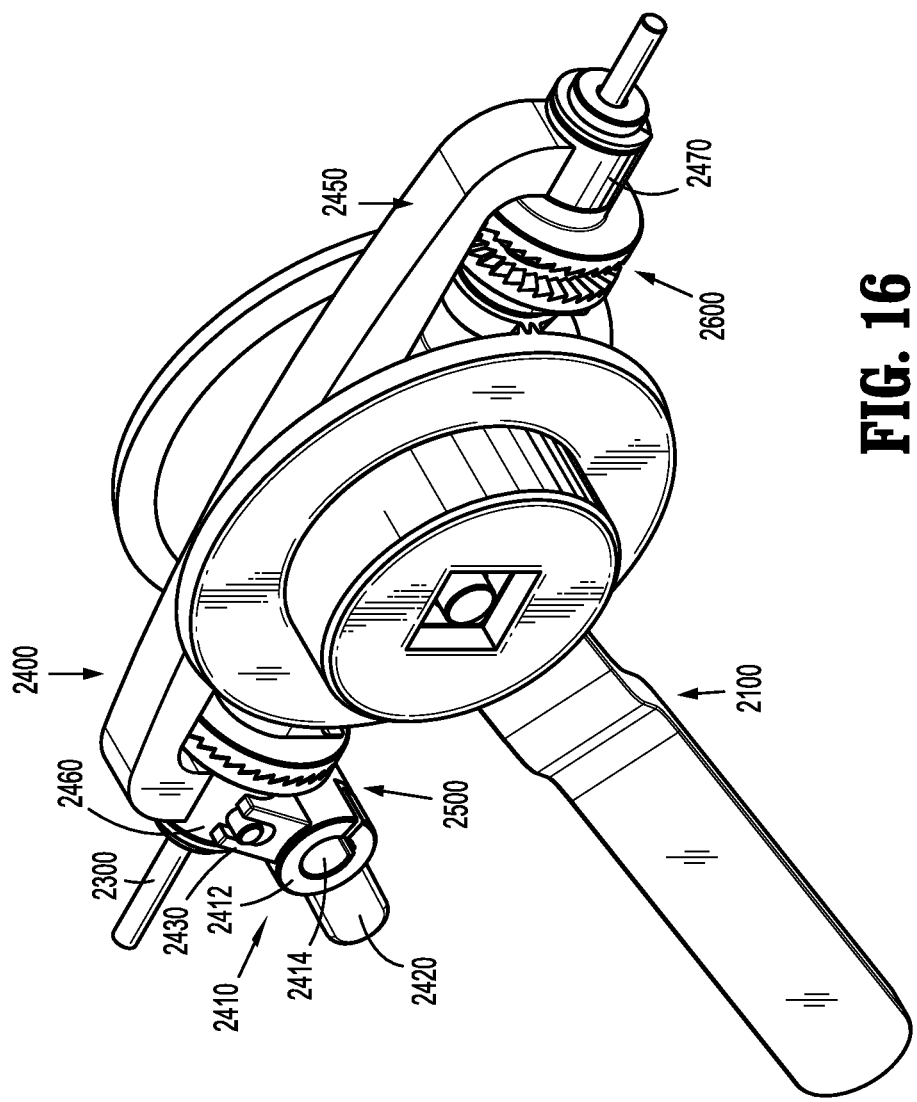
Figure 17:
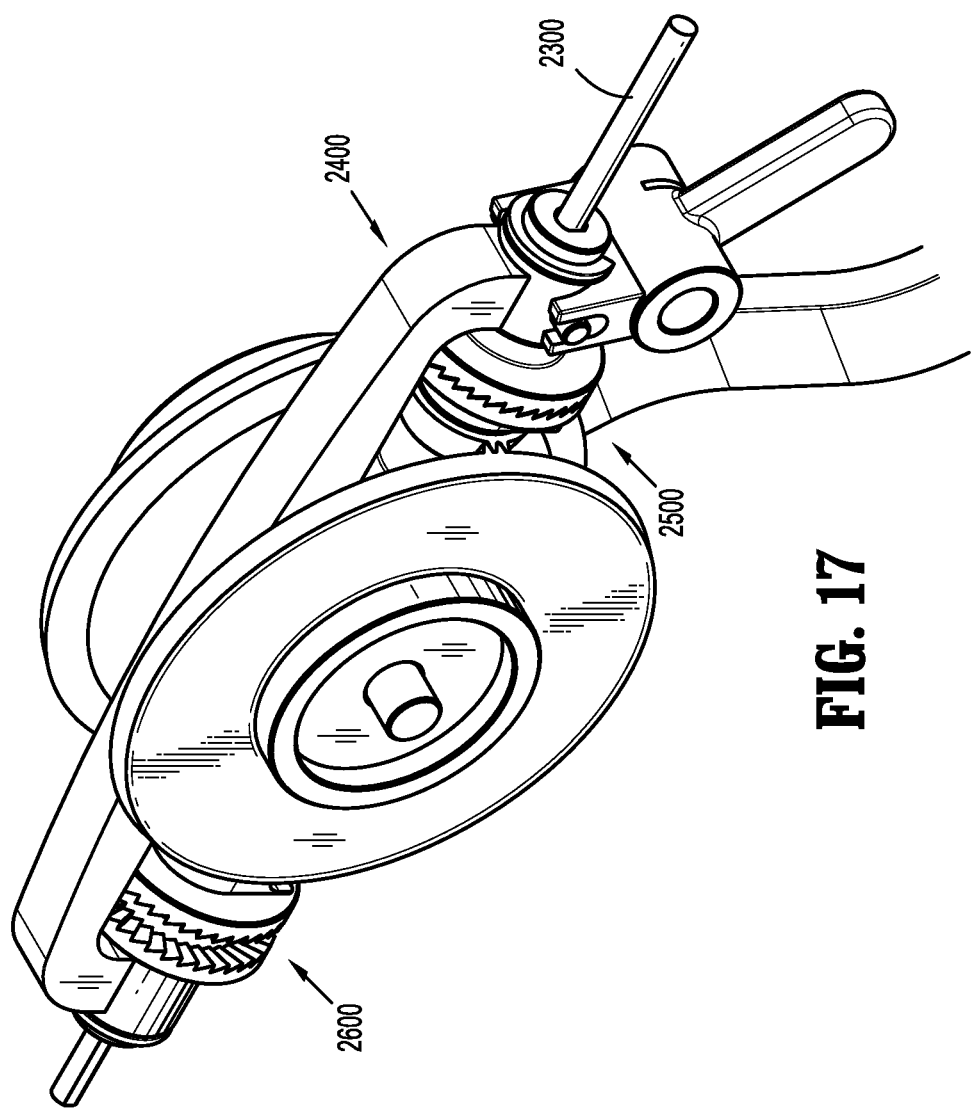
Figure 20:
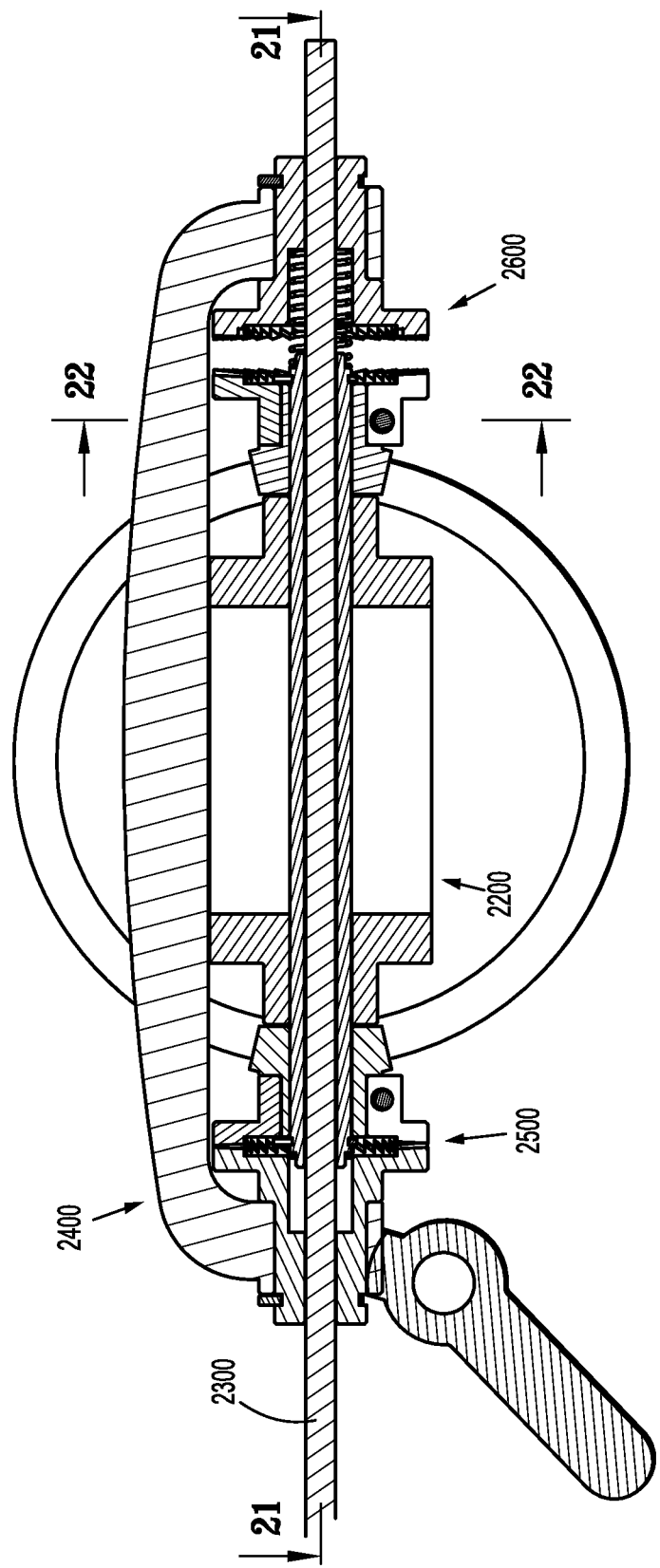
FIG. 20 is a longitudinal cross-sectional view of the third handle assembly taken along line 20-20 of FIG. 19.

Referring now to FIGS. 15, 16 and 24, switch assembly 2400 is shown including hand switch 2410 and switch bar or frame 2450. Switch assembly 2400 allows a user to selectively engage first distal gear 2520 with first proximal gear 2510, or second proximal gear 2610 with second distal gear 2620. As can be appreciated from the disclosure hereinabove, actuation of movable handle or lever 2110 during engagement between first distal gear 2520 and first proximal gear 2510 results in rotatable rod 2330 rotating in the substantial direction of arrow "J" (i.e., clockwise), whereas actuation of movable handle or lever 2110 during engagement between second proximal gear 2610 and second distal gear 2620 results in rotatable rod 2330 rotating in the substantial direction of arrow "K" (i.e., counter-clockwise).

Hand switch 2410 of switch assembly 2400 includes a cylindrical portion 2412 including an aperture 2414 extending at least partially therethrough, a lever 2420 depending from cylindrical portion 2412, and a pair of tines 2430 depending from cylindrical portion 2412. Switch bar 2450 includes a distal cylindrical portion 2460 configured to mechanically engage a distal portion 2522 of first distal gear 2520, a proximal cylindrical portion 2470 configured to mechanically engage a proximal portion 2612 of second proximal gear 2610, an elongated member 2480 interconnecting distal cylindrical portion 2460 and proximal cylindrical portion 2470, and a pair of pins 2490 extending from distal cylindrical portion 2460.

When positioned within a housing assembly 2010 (see FIGS. 25-29), cylindrical portion 2412 of hand switch 2410 is positioned in a pivotal relationship with housing assembly 2010 (e.g., a pin of housing assembly 2010 extends at least partially through cylindrical portion 2412), and each tine 2430 is mechanically engaged with each pin 2490. In the embodiment shown, lever 2420 of hand switch 2410 is in a first, distal position, which corresponds with first distal gear 2520 being mechanically engaged with first proximal gear 2510. Lever 2420 of hand switch 2410 is able to be actuated in the substantial direction of arrow "L" (FIG. 27) by a user, which causes tines 2430 to pivot distally. Distal movement of tines 2430 causes pins 2490, distal cylindrical portion 2460, elongated member 2480, and proximal cylindrical portion 2470 to move distally. Distal movement of distal cylindrical portion 2460 results in distal movement of first distal gear 2520, which causes first distal gear 2520 to disengage from first proximal gear 2510. Additionally, distal movement of proximal cylindrical portion 2470 results in distal movement of second proximal gear 2610 into mechanical engagement with second distal gear 2620. Thus, as can be appreciated, a user is able to toggle lever 2420 of hand switch 2410 to select whether actuation of movable handle or lever 2110 causes a clockwise rotation or a counter-clockwise rotation of rotatable rod 2330, and thus the direction of rotation of control rod 140. It is further envisioned that, lever 2420 is included on a one-way ratchet such that when lever 2420 is actuated in a first direction (e.g., to effect clockwise rotation of rotatable rod 2330), lever 2420 is prevented from moving in the opposite direction (which prevents a counter-clockwise rotation of rotatable rod 2330) until the end of the initial stroke in the first direction.

Figure 29:
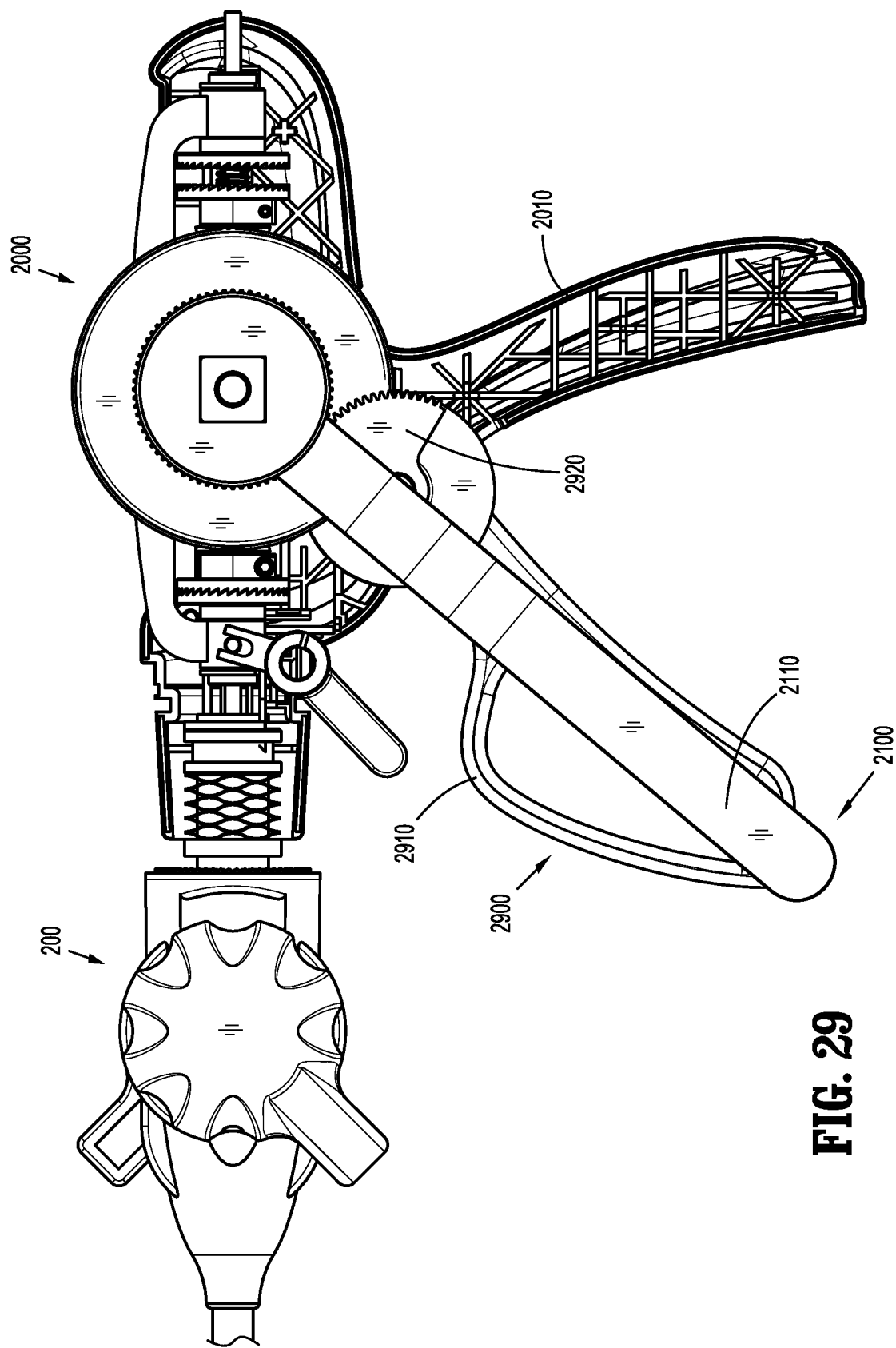
FIG. 29 is a side view, with parts removed, of the third handle assembly engaged with the control assembly and the handle housing, with the addition of an override handle.

With specific reference to FIGS. 25-28, control assembly 200 of surgical instrument 10 is shown engaged with third handle assembly 2000, but illustrates an alternate actuation assembly 2900 including an alternate movable handle or lever 2910 and a handle gear 2920. It is envisioned that third handle assembly 2000 can function similarly whether third handle assembly 2000 includes actuation assembly 2100 or alternate actuation assembly 2900. Additionally, FIG. 29 illustrates third handle assembly 2000 including both actuation assembly 2100 and alternate actuation assembly 2900. Here, it is envisioned that one of movable handle or lever 2110 or alternate movable handle or lever 2910 can act as an override handle.

Additionally, it is envisioned that housing assembly 2010 is similar to the housing assembly of second handle assembly 1000, described above, in that housing assembly 2010 can be configured to allow a user to separate or disconnect third handle assembly 2000 from control assembly 200 of surgical instrument 10. For example, it is envisioned that spring loaded lock/release mechanism 1200 of second handle assembly 1000 is also present on third handle assembly 2000.

Figure 30:
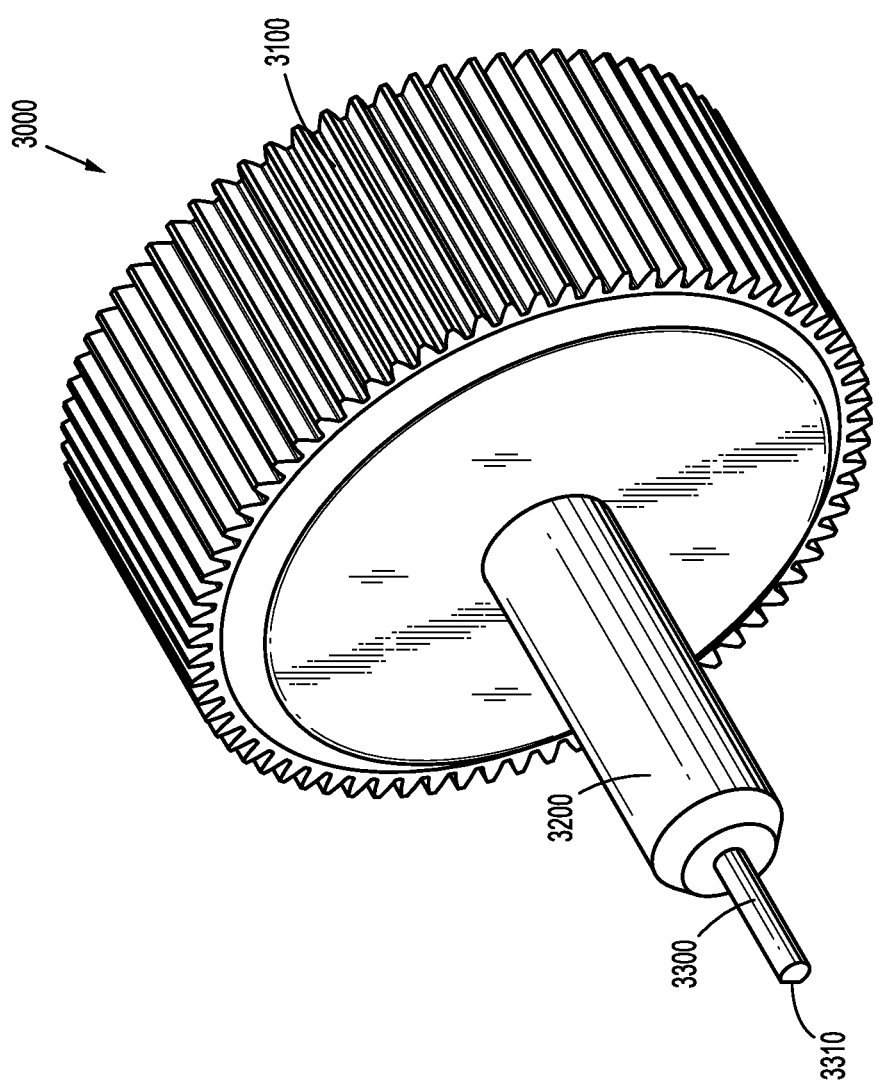
FIG. 30 is a perspective view of a bailout tool for used in connection with the surgical instrument of the present disclosure.

Referring now to FIG. 30, a fourth handle assembly or bailout tool 3000 of the present disclosure is shown. Bailout tool 3000 is configured to give a user an additional option to provide rotation to control rod 140 (e.g., after removing or disconnecting second handle assembly 1000 or third handle assembly 2000).

Bailout tool 3000 includes knob 3100, a first cylindrical portion 3200 extending from knob 3100, and a second cylindrical portion 3300 extending from first cylindrical portion 3200. Second cylindrical portion 3300 is configured to mechanically engage cavity 142 of control rod 140 of surgical instrument 10. A cross-section of cavity 142 is similarly- or complimentarily-shaped to the cross-section of second cylindrical portion 3300, such that a flat surface 3310 of second cylindrical portion 3300 engages a corresponding flat surface of cavity 142 to limit or prevent rotation therebetween. Thus, a user can align and insert second cylindrical portion 3300 into cavity 142 of control rod 140, and rotate knob 3100 in either a clockwise or a counter-clockwise direction to impart a corresponding rotational movement to control rod 140, to effect a desired function of end effector 500.

Accordingly, the present disclosure includes a surgical system including a surgical instrument 10, a control assembly 200, and a plurality of handle assemblies (e.g., first handle assembly 100, second handle assembly 1000, third handle assembly 2000, and fourth handle assembly 3000) for use with surgical instrument 10. As discussed above, first handle assembly 100 and second handle assembly 1000 are powered (e.g., via batteries), while third handle assembly 2000 and fourth handle assembly 3000 are manual (i.e., not powered). Accordingly, the disclosed system provides the user with a variety of options for conducting surgical procedures. Additionally, the disclosed system allows the user to remove a handle assembly (e.g., second handle assembly 1000) from surgical instrument 10 (e.g., while a portion of surgical instrument 10 remains within a patient), and engage another handle assembly (e.g., third handle assembly 2000 or fourth handle assembly 3000) with surgical instrument 10, to complete the surgical procedure, for instance.

Additional reference may be made to International Application No. PCT/US2008/077249, filed Sep. 22, 2008 (Inter. Pub. No. WO 2009/039506) and U.S. patent application Ser. No. 12/622,827, filed on Nov. 20, 2009 (U.S. Patent Publication No. 2011-0121049), the entire content of each of which is incorporated herein by reference, for a detailed description of the construction and operation of exemplary electromechanical, hand-held, powered surgical instruments.

The present disclosure also relates to a method of using the system described above. Moreover, the present disclosure includes a method of providing the surgical system disclosed herein, or components thereof, removing a handle assembly (e.g., a powered handle assembly, such as second handle assembly 1000) from surgical instrument 10, and mechanically engaging another handle assembly (e.g., a manual handle assembly, such as third handle assembly 2000 and/or fourth handle assembly 3000) with surgical instrument. The method also comprises conducting a first surgical procedure (or at least attempting a surgical procedure) with the powered handle assembly, and conducting a second surgical procedure with a manual handle assembly.

With reference to FIGS. 31-38, a cartridge assembly 5000 and components thereof are illustrated. Cartridge assembly 5000 is configured for use with a surgical instrument, e.g., at least one of the surgical instruments disclosed herein. Specifically, cartridge assembly 5000 is configured to engage the distal end of an elongated portion of a surgical instrument, such that a distal end of control rod (e.g., control rod 140) of the surgical instrument mechanically engages a lead screw 5100 of cartridge assembly 5000 (see FIG. 38). Generally, rotation of the control rod causes a corresponding rotation of lead screw 5100, which results in longitudinal translation of clamping member 5200, longitudinal translation of actuation sled 5300, movement of pushers 5400, and ejection of fasteners 5500. As further described below, cartridge assembly 5000 and various components thereof are configured to allow the distal end of the control rod and lead screw 5100 to be longitudinally aligned, and thus provide a direct transfer of rotation between the two components (e.g., without the use of an angle drive). Several modifications to a traditional cartridge assembly are required to accommodate this orientation.

The term "traditional" as used herein is to distinguish the features of the present disclosure from features that are not part of the present disclosure. The use of "traditional" is not acquiescing that those features are prior art. Additionally, while several figures include the features of the present disclosure alongside "traditional" features, the "traditional" features are shown for illustrative purposes; the actual embodiments of the present disclosure do not include the "traditional" features, and include two set of the disclosed features, where appropriate.

Figure 31:
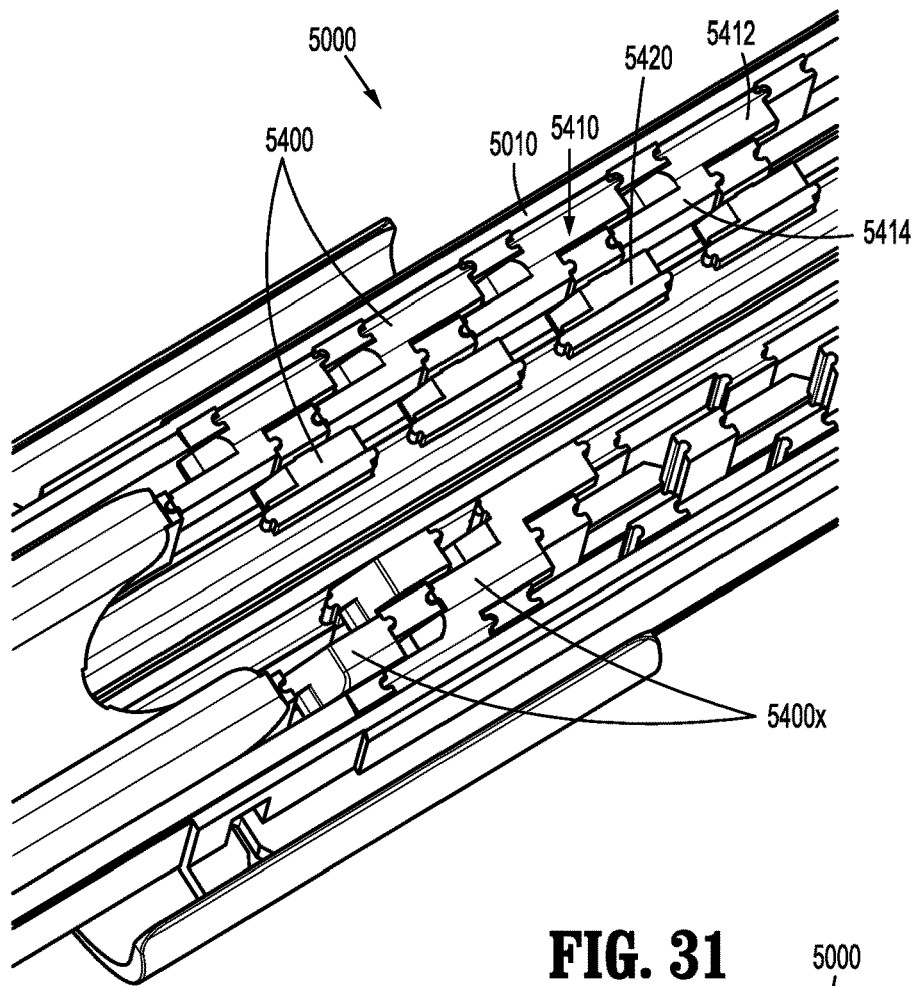
FIG. 31 is a perspective view of a lower portion of a cartridge assembly showing two sets of pushers.
Figure 33:
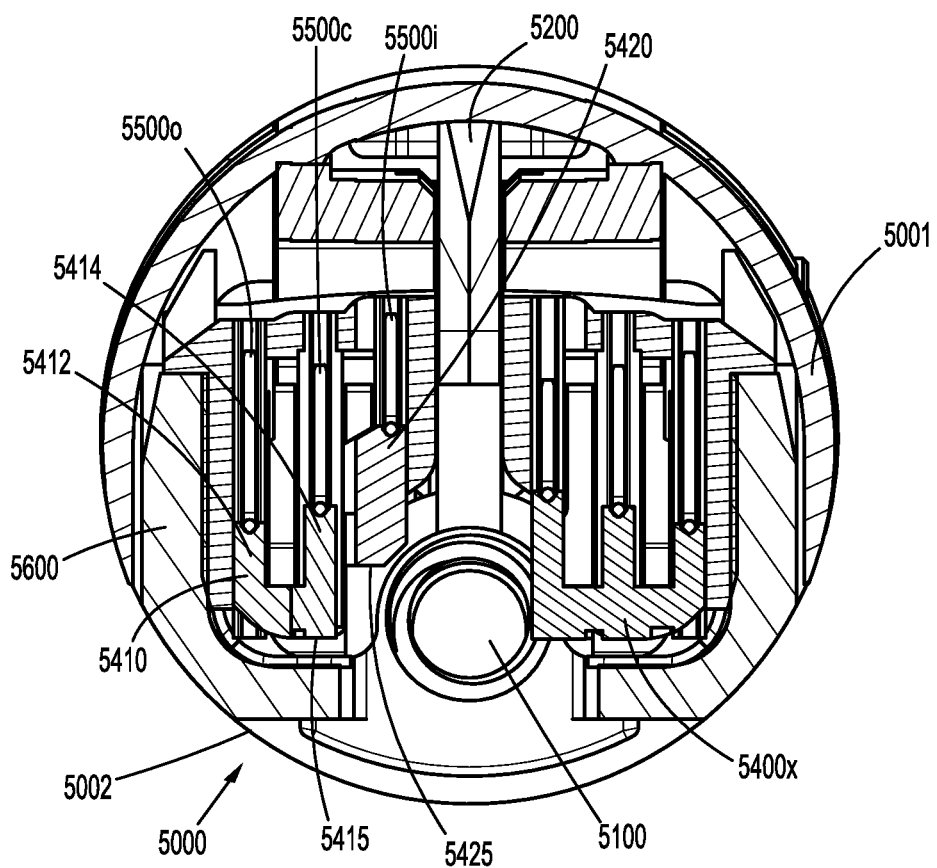
FIG. 33 is a cross-sectional view of the cartridge assembly of FIG. 32 and an anvil assembly.

With initial reference to FIGS. 31 and 33, modified pushers 5400 are shown in additional to traditional pushers 5400x on the same cartridge assembly 5000. FIG. 33 also shows an anvil assembly 5001 in close proximity to cartridge assembly 5000. Specifically, pushers 5400 include sets of double pushers 5410 and sets of single pushers 5420, while traditional pushers 5400x include sets of triple pushers. Each double pusher 5410 includes an outer pusher 5412, which aligns with an outer fastener 5500o, and a central pusher 5414, which aligns with a central fastener 5500c. Each single pusher 5420 aligns with an inner fastener 5500i. As shown in FIGS. 31 and 33, outer pusher 5412 and central pusher 5414 of double pusher 5410 are joined, and are thus not free to move with regard to each other; single pusher 5420 is not connected to double pusher 5410, and is thus free to move with respect to an adjacent double pusher 5420, and is independently movable with respect to double pushers 5410. Additionally, as shown in FIG. 33, the base 5425 of single pusher 5420 (i.e., the portion farthest from inner fastener 5500i) is on a higher plane with respect to the base 5415 of double pusher 5410. As can be appreciated with regard to FIG. 33, the elevated height of the base 5425 of single pusher 5420 enables the full circumference of set screw 5100 to longitudinally pass through cartridge assembly 5000 (as compared to the traditional pushers 5400x illustrated on the right side in FIG. 33). It is further envisioned that the height of fastener 5500i is smaller than the height of fasteners 5500o and 5500c.

Figure 32:
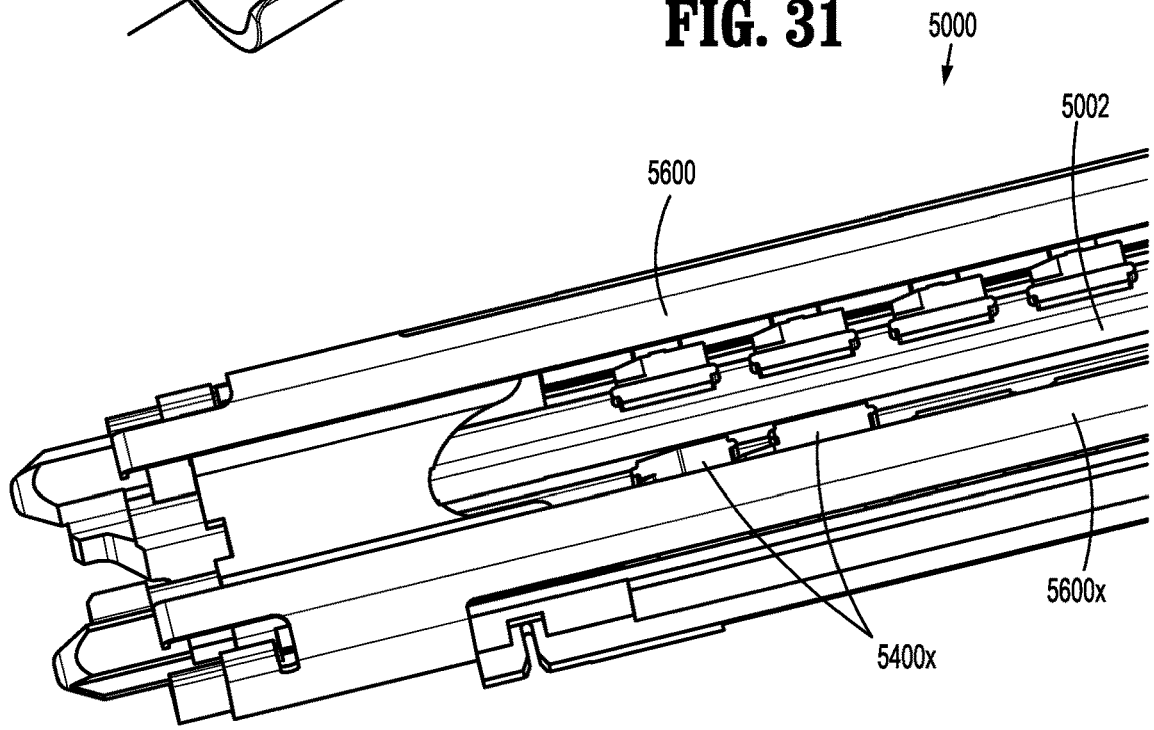
FIG. 32 is a perspective view of a lower portion of the cartridge assembly of FIG. 31 and including a pusher cover.

Referring now to FIG. 32, a pusher cover 5600 is shown. In FIG. 32, pusher cover 5600 of the present disclosure is shown on the top portion of cartridge assembly 5000, while a traditional pusher cover 5600x is shown on the lower portion. Pusher cover 5600 mechanically engages the base 5010 (see FIG. 31) of cartridge assembly 5000 and is configured to prevent double pushers 5410 from falling through the bottom 5002 of cartridge assembly 5000. As shown, single pushers 5420 are not protected by pusher cover 5600 because bases 5425 of single pushers 5420 are elevated, because lead screw 5100 would interfere with an inward extension of pusher cover 5600 (see FIG. 33), and because single pushers 5420 would interfere with the longitudinal travel of actuation sled 5300. Thus, single pushers 5420 must be otherwise maintained within cartridge assembly 5000.

Figure 35:
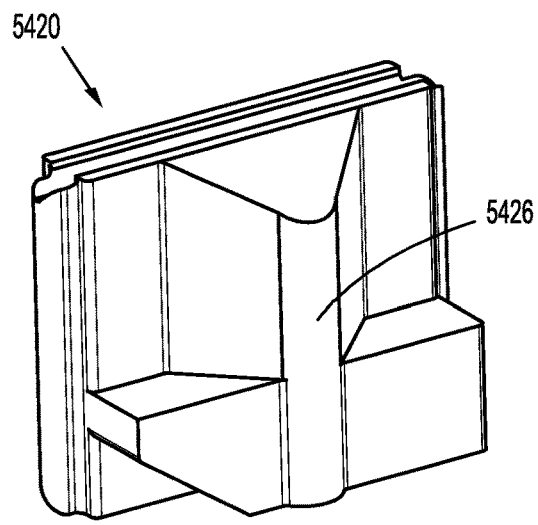
FIG. 35 is a perspective view of an inner staple pusher in accordance with an embodiment of the present disclosure.
Figure 36:
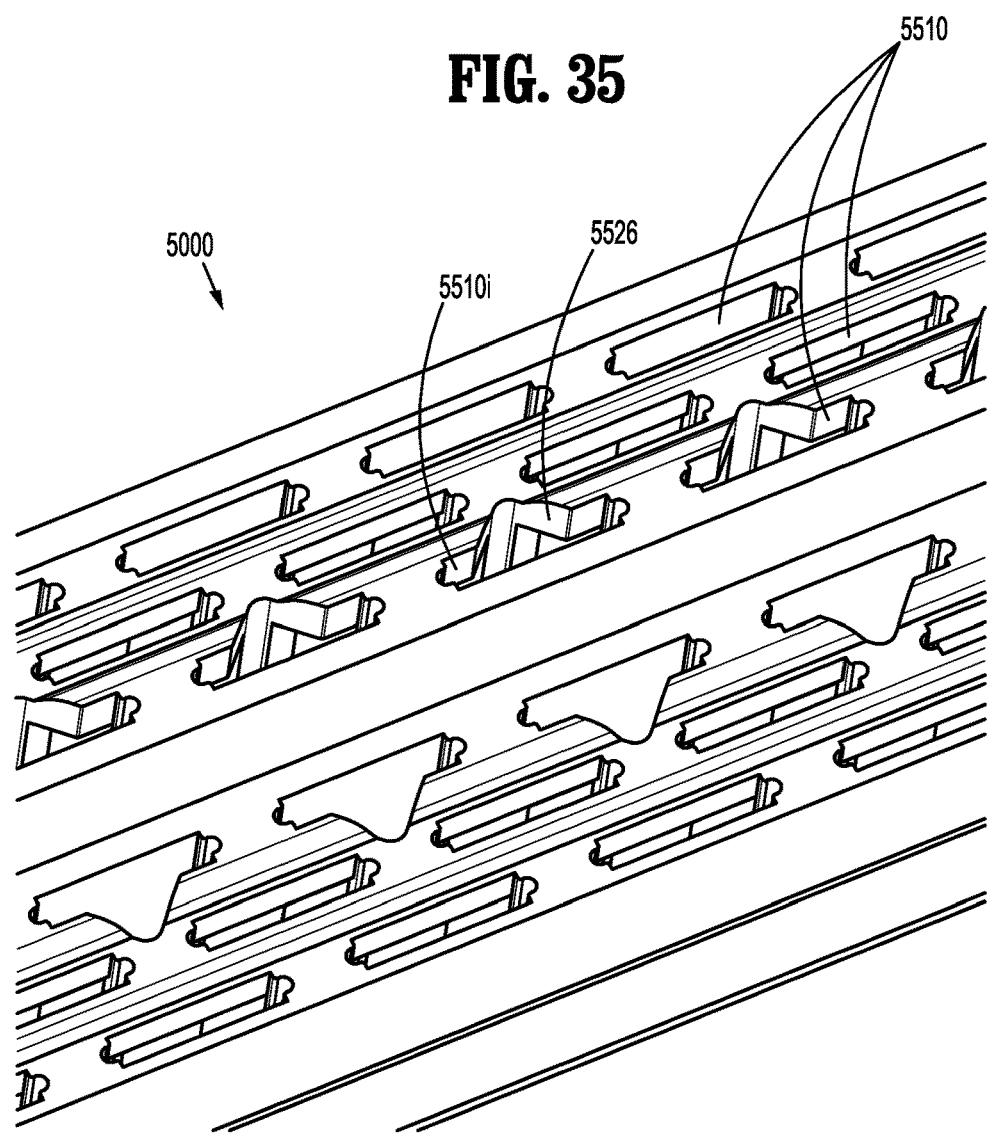
FIG. 36 is a perspective view of an upper portion of the cartridge assembly of FIGS. 31 and 32.

FIGS. 35 and 36 help illustrate how single pushers 5420 are maintained within cartridge assembly 5000. FIG. 35 illustrates single pusher 5420 having a nub or rib 5426 extending therefrom. FIG. 36 illustrates cartridge assembly 5000 including slots 5510 for accepting fasteners 5500. As shown, each inner slot 5510i includes a cut-out or channel 5526, which is configured to receive nub or rib 5426 of single pusher 5420. In combination with ribs 5426 and channels 5526, the installation of pushers 5400 helps maintain single pushers 5420 within cartridge assembly 5000. Single pushers 5420 are initially inserted into cartridge assembly 5000, such that a cartridge leg is able to flex out of the way of the ribs 5426. Next, the double pushers 5410 are inserted and at least partially fill the space behind the cartridge leg, which inhibits flexure of the cartridge leg. The single pushers 5420 are now effectively prevented from falling out of the bottom 5002 of the cartridge assembly 5000.

Figure 34:
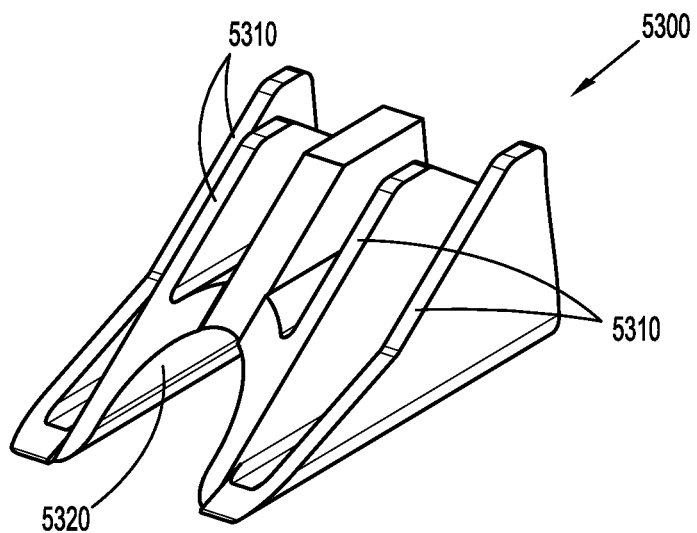
FIG. 34 is a perspective view of an actuation sled for use with the cartridge assembly of the present disclosure.
Figure 37:
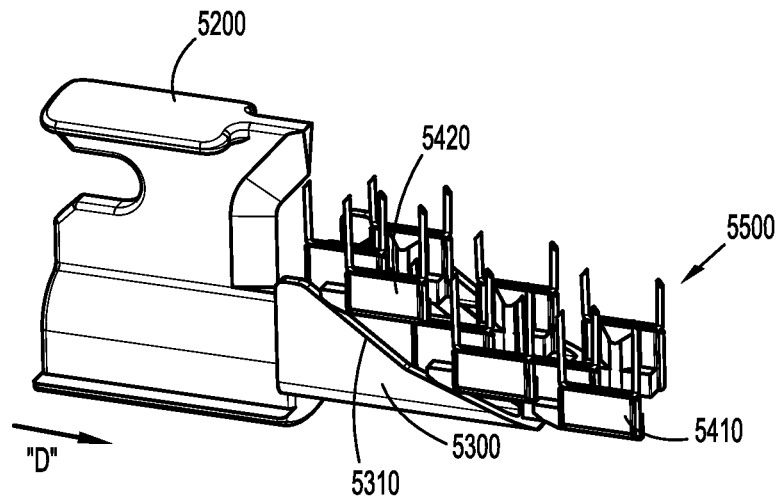
FIG. 37 is a perspective view of a clamping member, the actuation sled of FIG. 34, a plurality of staple pushers and staples in accordance with an embodiment of the present disclosure.
Figure 38:
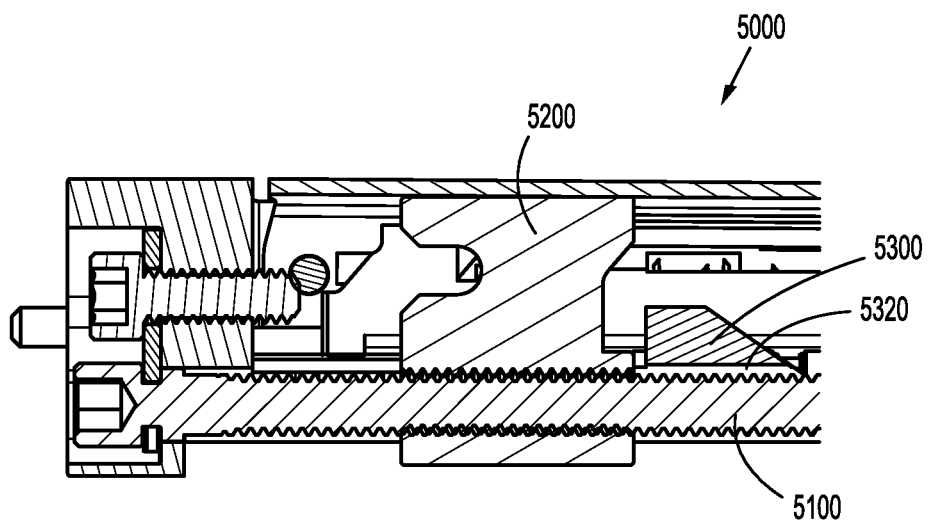
FIG. 38 is a cross-sectional view of a portion of the cartridge assembly of FIGS. 31 and 32 illustrating a lead screw extending longitudinally therethrough.

With reference to FIGS. 34, 37 and 38, actuation sled 5300 is illustrated. As shown, actuation sled 5300, which longitudinally translates at least partially through cartridge assembly 5000, includes cam surfaces 5310 for contacting pushers 5400, and includes an arched portion 5320 to accommodate lead screw 5100 to pass therethrough. As shown in FIG. 37, distal translation of clamping member 5200 in the direction of arrow "D" causes distal translation of actuation sled 5300 into pushers 5410 and 5420, and causes fasteners 5500 to be ejected from cartridge assembly 5000.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

The invention claimed is:

1. A surgical system, comprising:
a surgical instrument comprising a shaft assembly defining a longitudinal axis, an end effector disposed adjacent a distal portion of the shaft assembly, and a control rod disposed at least partially within the shaft assembly and being disposed in mechanical cooperation with the end effector, wherein actuation of the control rod effects a function of the end effector;
a first handle assembly configured for selective mechanical engagement with the control rod, the first handle assembly including a power source associated therewith, wherein actuation of the first handle assembly causes rotation of the control rod with respect to the longitudinal axis; and
a second handle assembly configured for selective mechanical engagement with the control rod, the second handle assembly including a switch assembly and a rod, the rod mechanically engagable with the control rod of the surgical instrument, the switch assembly configured to control the direction of rotation of the rod, the second handle assembly being manually operable and being free from association with a power source, wherein actuation of the second handle assembly causes rotation of the control rod with respect to the longitudinal axis, wherein the second handle assembly includes a first set of gears and a second set of gears, wherein rotation of the first set of gears, when engaged, causes rotation of the rod in the first direction to effect a first function of the end effector, wherein rotation of the second set of gears, when engaged, causes rotation of the rod in the second direction to effect a second function of the end effector, wherein the switch assembly allows a user to selectively engage the first set of gears without engaging the second set of gears, wherein the switch assembly allows a user to selectively engage the second set of gears without engaging the first set of gears, and wherein at least a portion of the switch assembly is movable in a direction parallel to the longitudinal axis relative to the shaft assembly to cause selective engagement between one of the first set of gears or engagement between the second set of gears,
wherein the first handle assembly is removable from engagement with the surgical instrument and is replaceable by the second handle assembly such that only one of the first handle assembly or the second handle assembly is engaged with the surgical instrument at a time,
wherein the first set of gears includes a first gear rotatable about the longitudinal axis and a second gear rotatable about the longitudinal axis, and wherein the second set of gears includes a first gear rotatable about the longitudinal axis and a second gear rotatable about the longitudinal axis.

2. The surgical system of claim 1, wherein the surgical instrument further comprises a manual articulation control configured to move the end effector at an angle with respect to the longitudinal axis.

3. The surgical system of claim 1, further comprising a third handle assembly configured for selective mechanical engagement with the control rod, the third handle assembly being manually operable and being free from association with a power source, only one of the first handle assembly, the second handle assembly or the third handle assembly is engaged with the surgical instrument at a time.

4. A surgical system, comprising:
a surgical instrument comprising a proximal portion, a distal portion, a shaft assembly defining a longitudinal axis, an end effector disposed adjacent a distal portion of the shaft assembly, and a control rod disposed at least partially within the shaft assembly and being disposed in mechanical cooperation with the end effector, wherein actuation of the control rod effects a function of the end effector;
a first handle assembly configured for selective mechanical engagement with the control rod, the first handle assembly including a power source associated therewith, wherein actuation of the first handle assembly causes rotation of the control rod with respect to the longitudinal axis; and
a second handle assembly configured for selective mechanical engagement with the control rod, the second handle assembly including a switch assembly and a rod, the rod mechanically engagable with the control rod of the surgical instrument, the switch assembly configured to control the direction of rotation of the rod, the second handle assembly being manually operable and being free from association with a power source, wherein actuation of the second handle assembly causes rotation of the control rod with respect to the longitudinal axis, wherein the second handle assembly includes a first set of gears and a second set of gears, wherein rotation of the first set of gears, when engaged, causes rotation of the rod in the first direction to effect a first function of the end effector, wherein rotation of the second set of gears, when engaged, causes rotation of the rod in the second direction to effect a second function of the end effector, wherein the switch assembly allows a user to selectively engage the first set of gears without engaging the second set of gears, wherein the switch assembly allows a user to selectively engage the second set of gears without engaging the first set of gears, wherein at least a portion of the switch assembly is movable in a proximal direction relative to the shaft assembly to cause a first portion of the switch assembly to engage the first set of gears, and wherein at least a portion of the switch assembly is movable in a distal direction relative to the shaft assembly to cause a second portion of the switch assembly to engage the second set of gears,
wherein the first handle assembly is removable from engagement with the surgical instrument and is replaceable by the second handle assembly such that only one of the first handle assembly or the second handle assembly is engaged with the surgical instrument at a time,
wherein the first set of gears includes a first gear rotatable about the longitudinal axis and a second gear rotatable about the longitudinal axis, and wherein the second set of gears includes a first gear rotatable about the longitudinal axis and a second gear rotatable about the longitudinal axis.

* * * * *